United States Patent
Dodds et al.

(10) Patent No.: US 9,005,207 B2
(45) Date of Patent: Apr. 14, 2015

(54) SURGICAL INSTRUMENT

(75) Inventors: Gordon Dodds, Feldkirchen (DE);
Harald Bornfleth, Feldkirchen (DE);
Kevin Booth, Leeds (GB); Liam Dower,
Leeds (GB); Dan Auger, Warsaw, IN
(US)

(73) Assignee: Depuy International Limited, Leeds
(GB)

( * ) Notice: Subject to any disclaimer, the term of this
patent is extended or adjusted under 35
U.S.C. 154(b) by 381 days.

(21) Appl. No.: 12/665,820

(22) Filed: Dec. 21, 2009

(65) Prior Publication Data

US 2011/0245835 A1    Oct. 6, 2011

(51) Int. Cl.
| | |
|---|---|
| A61B 17/58 | (2006.01) |
| A61B 17/60 | (2006.01) |
| A61F 2/00 | (2006.01) |
| A61B 17/15 | (2006.01) |
| A61B 17/17 | (2006.01) |
| A61B 19/00 | (2006.01) |

(52) U.S. Cl.
CPC ........... *A61B 17/155* (2013.01); *A61B 17/1764*
(2013.01); *A61B 2019/307* (2013.01)

(58) Field of Classification Search
USPC .................................. 606/79, 82, 86 R–90
See application file for complete search history.

(56) References Cited

U.S. PATENT DOCUMENTS

| | | | |
|---|---|---|---|
| 5,688,279 A * | 11/1997 | McNulty et al. ................. 606/88 |
| 5,925,049 A * | 7/1999 | Gustilo et al. ................... 606/82 |
| 6,013,081 A * | 1/2000 | Burkinshaw et al. ........... 606/88 |
| 2004/0260301 A1 | 12/2004 | Lionberger | |
| 2005/0203528 A1* | 9/2005 | Couture et al. ................. 606/86 |
| 2005/0234461 A1 | 10/2005 | Burdulis | |
| 2006/0195111 A1 | 8/2006 | Couture | |
| 2009/0088754 A1* | 4/2009 | Aker et al. ...................... 606/79 |
| 2009/0131941 A1* | 5/2009 | Park et al. ....................... 606/87 |

FOREIGN PATENT DOCUMENTS

| | | |
|---|---|---|
| EP | 1669033 A1 | 6/2006 |
| WO | WO 9832384 A1 | 7/1998 |
| WO | WO 2005110250 A1 | 11/2005 |

OTHER PUBLICATIONS

UK Search Report GB0712290.6 dated Sep. 20, 2007.
PCT International Search Report and Written Opinion PCT/GB2008/002181 dated Sep. 24, 2008.

* cited by examiner

*Primary Examiner* — Kevin T Truong
*Assistant Examiner* — Samuel Hanna

(57) ABSTRACT

Patient specific surgical instruments, and in particular cutting guides, and methods of use and manufacture are described. The surgical instrument can be used in an orthopaedic arthroplasty procedure to be carried out on a joint of a patient and can allowing soft tissue balancing for the joint. The instrument comprises a body having an attachment area configured using data specific to a bone of the joint of the patient so as to attach to the bone in a unique position. The instrument includes at least a first cutting guide and an adjustment mechanism operable to change the position of the cutting guide relative to the bone.

6 Claims, 20 Drawing Sheets

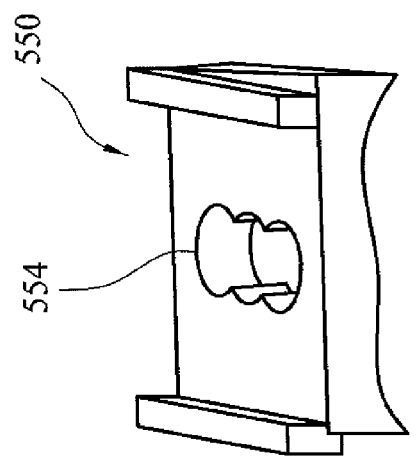
FIG. 14D
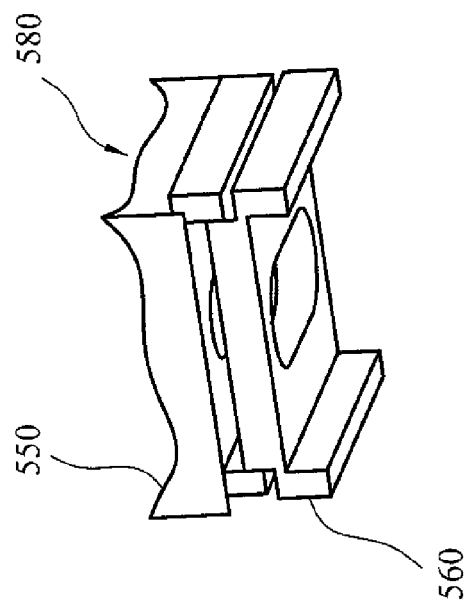
FIG. 14G
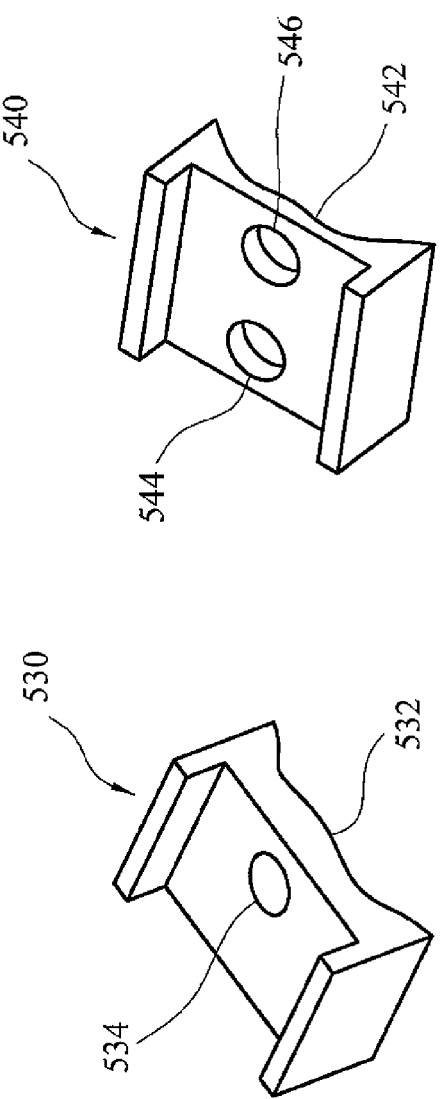
FIG. 14C
FIG. 14F
FIG. 14B
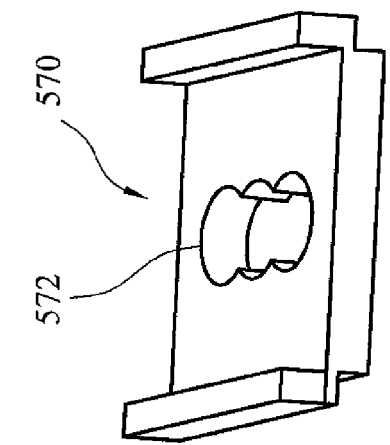
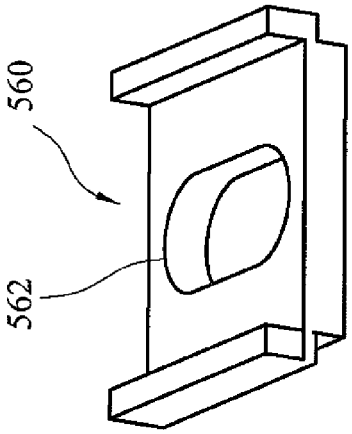
FIG. 14E

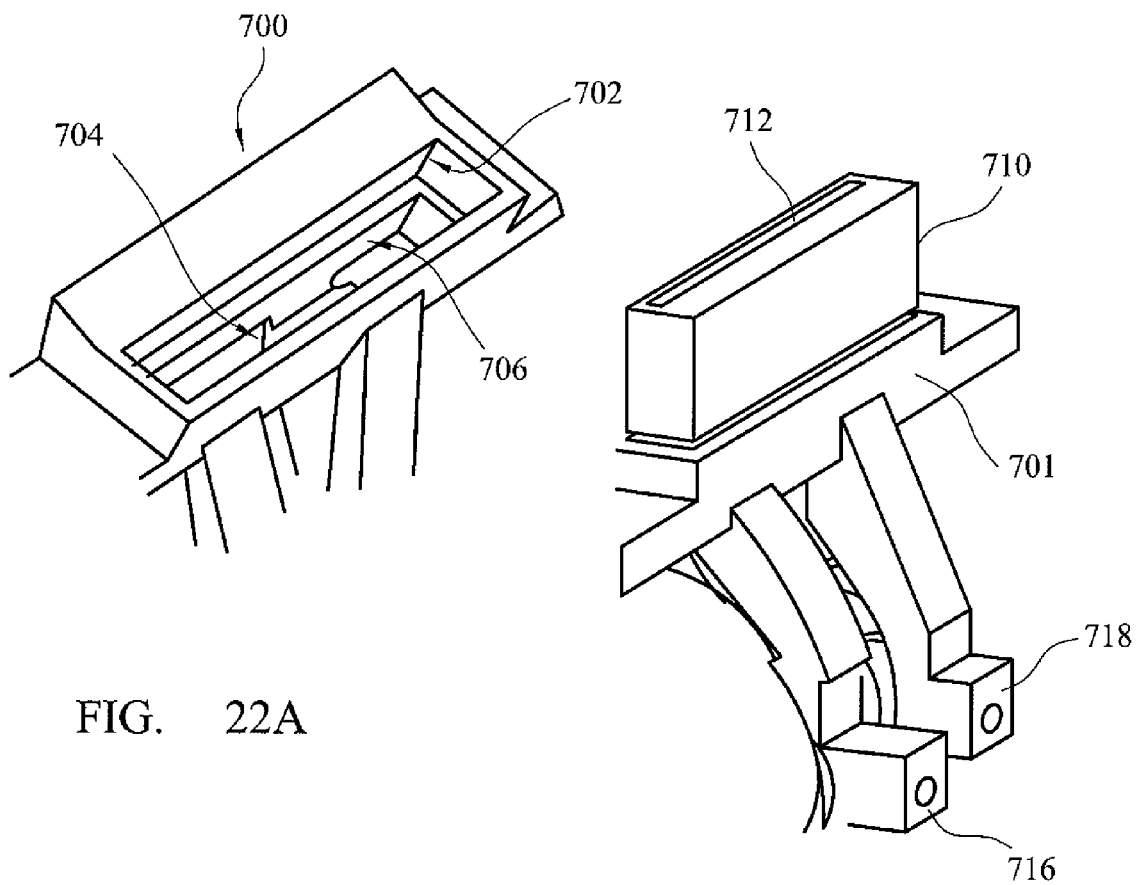
FIG. 22A
FIG. 22B
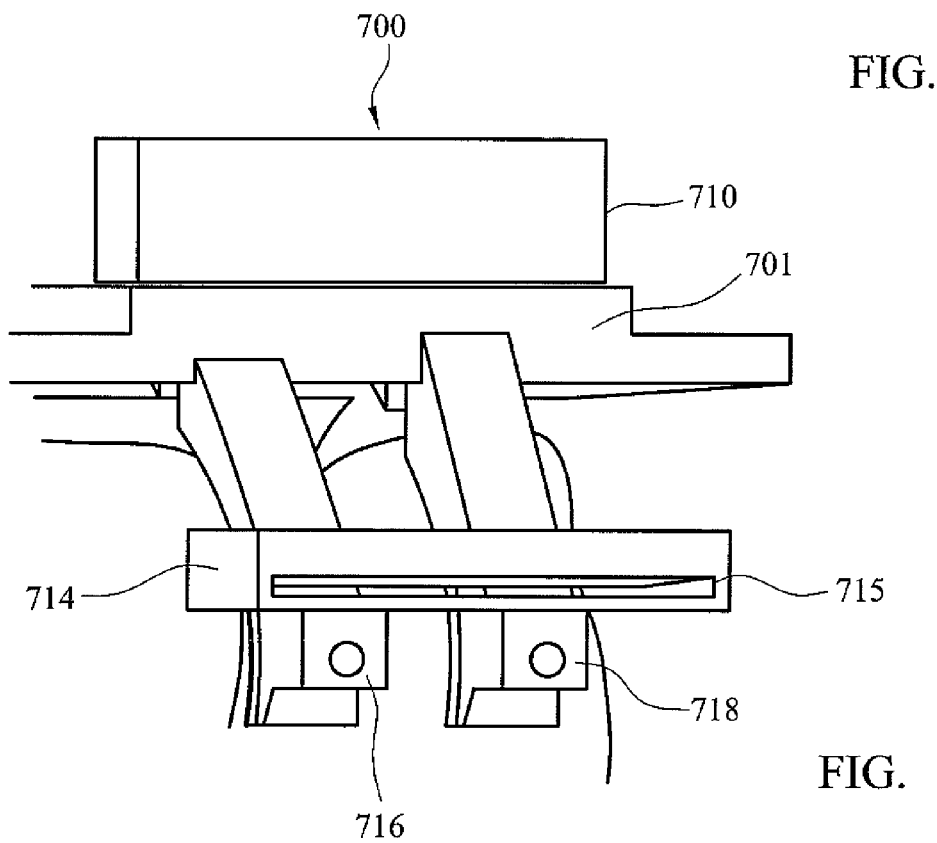
FIG. 22C

SURGICAL INSTRUMENT

CROSS REFERENCE TO RELATED APPLICATION

This application is a National Stage 35 U.S.C. 371 of International Patent Application PCT/GB2008/002181 filed Jun. 25, 2008.

FIELD OF THE INVENTION

The present invention relates to surgical instruments, and in particular to a cutting guide which can be used in orthopaedic arthroplasty procedures to allow soft tissue balancing.

BACKGROUND OF THE INVENTION

Orthopaedic arthroplasty procedures often involve the use of an implant or implants which is used to replace an articulating surface or surfaces of the joint. Usually such implants are attached to a resected or otherwise prepared part of a patient's bone. A cutting guide can be attached to the patient's bone to allow surfaces of the bone to be resected to accept the implant. A variety of approaches are available to planning, guiding and placing the cutting guides, implants and other instruments used during the procedure, so as to try and ensure that the joint is correctly rebuilt. However, for some joints, such as the knee joint, it is also necessary to take into account the soft tissue structures of the joint, such as the ligaments, so as to try and ensure that the joint is correctly rebuilt.

Computer Assisted Surgery (CAS) systems can be used to plan and navigate the position of cutting guides, implants, etc in order to try and take into account soft tissue structures. The planned position of a cutting guide can be updated intra-operatively based on measurements of the soft tissues in order to adjust the cuts to be made to the bone to change the eventual position of the implant. However, CAS systems are expensive and are not widely available. Further some surgeons prefer not to use CAS systems and prefer to use their own workflow and techniques.

A non-navigated approach to positioning a cutting guide can be achieved by producing a patient specific cutting guide using data from captured images of a patient's bone (sometimes referred to as "templating") so that the cutting guide can be attached in a predefined position to the patient's bone thereby fixing the position of the cuts in the planned position. However, this approach is not suitable for allowing soft tissues to be taken into account as the position of the cuts relative to the patient's bone is fixed pre-operatively. The actual cuts that may be required in order to take into account the soft tissue structures of the joint or for other reasons may only become apparent intra-operatively and so the cuts defined by the cutting guide are non-optimal.

The present invention provides a mechanism allowing intra-operatively available soft tissue information, or other information, to be used to make the correct cuts, without requiring a complex planning or navigation system.

SUMMARY OF THE INVENTION

According to a first aspect of the present invention, there is provided a device or instrument for use in an orthopaedic procedure on a joint of a patient. The device can allow soft tissue balancing for the joint. The device comprises a body, at least one attachment area, the or each attachment area being configured to be a specific match to a bone of the joint of the patient so as to attach to the bone in a unique position, at least a first cutting guide and an adjustment mechanism operable to change the position of the cutting guide.

Hence, the patient specific attachment areas automatically navigate the device so that it is attached to the bone in a predetermined position. However, the cuts to be made to the bone can then be adjusted so as to help provide at least some soft tissue balancing. Hence, no complex navigation system is needed and the ability to tailor the bone cuts to compensate for soft tissues of the joint is provided.

The adjustment mechanism can be operable to change the position of the cutting guide. relative to the bone while the instrument is attached to the bone by the attachment areas.

The adjustment mechanism can be operable to change the position of the cutting guide. relative to the bone prior to attaching the instrument to the bone by the attachment areas.

The adjustment mechanism can allow the cutting guide to be translated. The adjustment mechanism can allow the or each cutting guide, or some of the cutting guides, to be translated in the anterior-posterior direction and/or the medial-lateral direction and/or the superior-inferior direction.

The adjustment mechanism can allow the cutting guide to be rotated. The adjustment mechanism can allow the or each cutting guide, or some of the cutting guides, to be rotated about the anterior-posterior direction and/or the medial-lateral direction and/or the superior-inferior direction.

The adjustment mechanism can allow translation and/or rotation of the or each cutting guide.

The instrument can include a plurality of adjustment mechanisms of the types mentioned above and below.

The adjustment mechanism can comprise a crumple zone. The adjustment mechanism can comprise a part of the instrument which has been engineered to allow the form, shape or configuration of the instrument to be deformed.

The adjustment mechanism can include a plurality of holes for accepting a fixing, such as attachment pins or screws. The plurality of holes can be in the body. Multiple groups of a plurality of holes can be provided.

The instrument can include at least one or more break away parts. The instrument can be engineered to allow one or more parts of the instrument, particularly parts which contact the bone, to be broken away from the instrument in a specific manner.

The adjustment mechanism can comprise at least one or a plurality of adjustment screws. The body can be mounted to the plurality of attachment areas by the or each adjustment screw.

The adjustment mechanism can comprise a plurality of spacers. The spacers can be removably attachable to the attachment areas.

The adjustment mechanism can comprise at least one or a plurality of screws each having a foot bearing one, or a plurality, of the plurality of attachment areas.

The instrument can include a plurality of different cutting guides. The plurality of different cutting guides can be borne by the body.

The or each cutting guide can be adapted to receive a cutting device or part thereof in use. The cutting device, or part thereof, can be a saw blade, or a milling device.

The or each cutting guide can be adapted and/or positioned and/or located and/or angled to allow a tibial cut or a femoral cut to be made to the bone guided by the cutting guide.

The instrument can be adapted or configured to be attachable to a proximal or distal end of a femur or a tibia The instrument can include at least one break away part which can be removed to allow the cutting guide and/or instrument to be moved relative to the bone to change the position of the cutting guide.

The adjustment mechanism can be operable to move the or each cutting guide relative to the bone.

The adjustment mechanism can comprise a recessed portion of the body and at least one insert to be received in the recess and having a formation defining a cutting guide. The formation can be a slot. A plurality of inserts can be provided. The slot in each insert can have a different position and/or angle in the insert.

The adjustment mechanism can include a caming surface and a cam follower which interact to separate the body and at least one attachment area of the instrument. The caming surface can be a sloped surface. The cam follower can be a sloped surface. The caming surface and cam follower can be generally wedge shaped members. A one of the camming surface and cam follower can be stationary and the other can be movable by a drive mechanism.

The adjustment mechanism can include a pivot mechanism operable to allow the angle of the cutting guide to be adjusted.

The adjustment mechanism can include a plurality of cutting guides intended for making the same cut and a barrier member or members for preventing use of all of the cutting guides. The barrier member can allow only a one of the cutting guides to be used.

The adjustment mechanism can include a plurality of spacers. The spacers can be removably attachable, e.g. push fit attachable, to the body and/or a component bearing an attachment surface.

The adjustment mechanism can include a crumple zone having a plurality of apertures allowing the material of the mechanism to collapse. The adjustment mechanism can include one or a plurality of removable support members, such as a prop or wedge, insertable into at least some of the plurality of apertures to prevent collapse and removable to allow collapse.

The adjustment mechanism can include a plurality of apertures for receiving fasteners. The plurality of apertures can comprise a plurality of groups of a plurality of apertures. Each group of a plurality of apertures can comprise a plurality of sub-groups of a plurality of apertures allowing adjustment in different directions and/or angle.

A single attachment area can be provided. The attachment area may extend over a significant portion of the instrument to allow unique attachment of the instrument to the bone. The single attachment area can be configured to attach to a plurality of different and/or separate anatomical features or areas of the bone.

The instrument can have a plurality of attachment areas. Sufficient separate attachment areas can be provided to uniquely attach the instrument to the bone. The plurality of attachment areas can engage the bone on at least five different positions of the surface of the bone. Preferably at least three different attachment areas are provided, more preferably at least four different attachment areas and most preferably five, or at least five, different attachment areas are provided. At least seven or seven attachment areas can also be used. At least one of the attachment areas can contact the side of the bone and at least one of the attachment areas can contact the end of the bone.

According to a further aspect of the invention there is provided a method for carrying out an orthopaedic procedure on a joint of a patient and providing soft tissue balancing for the joint. The method can comprise providing a device having a body including a plurality of attachment areas, the plurality of attachment areas being configured to be a specific match to a bone of the joint of the patient so as to attach to the bone in a unique position, attaching the device to the bone by engaging the plurality of attachment areas with the surface of the bone; and operating an adjustment mechanism of the instrument to change the position of a cutting guide of the device.

The position of the cutting guide can be changed while the body is attached to the bone by the attachment areas.

According to a further aspect of the invention, there is provided a method of manufacturing a device, comprising capturing data specifying the shape of a bone of a joint of a patient from the patient, and manufacturing at least the attachment area of a device according to the first aspect of the invention, using the captured data. Preferably, the data is captured using an imaging technique, for example, a CT scan.

BRIEF DESCRIPTION OF THE DRAWINGS

Embodiments of the invention will now be described, by way of example only, and with reference to the accompanying drawings, in which:

FIGS. 14A to 14G show perspective views of a part of further embodiment of an instrument according to the invention and spacers components for use with the instrument;

FIGS. 22A to 22F show perspective views of a further embodiment of an instrument according to the invention and insert blocks used as part of the adjustment mechanism of the instrument;

DETAILED DESCRIPTION OF THE DRAWINGS

Figure 1:
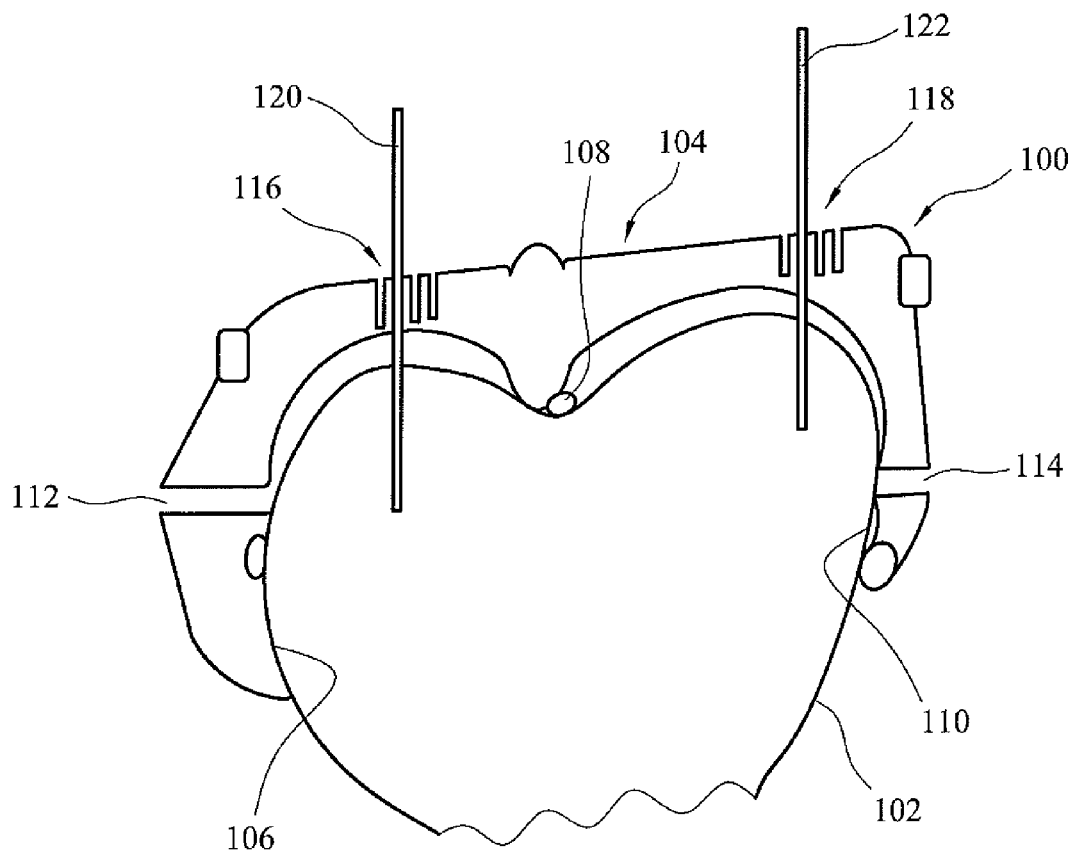
FIG. 1 shows a schematic cross sectional view through a first embodiment of a surgical instrument according to the invention.

Similar items in different Figures share common reference numerals unless indicated otherwise.

FIG. 1 shows a schematic cross-sectional view through a first embodiment of a surgical instrument 100 according to the present invention, mounted on the proximal tibia or distal femur 102. In FIG. 1, the cross-section is shown in the coronal plane. The instrument 100 has a main body part 104 and a number of attachment areas 106, 108, 110 by which the instrument engages the proximal part of the tibia or distal femur 102. Aligned slots 112, 114 are borne by the body 104 and provide a first cutting guide for accepting a saw blade in use to resect the bone 102. Other slots are also provided in the body for making other cuts to the femur or tibia, as required when preparing the bone for an implant, but are not shown in FIG. 1, for the sake of clarity. The instrument 100 also includes a first group of four holes 116 and a second group of four holes 118 which in use can accept bone pins 120, 122 as illustrated in FIG. 1.

Pre-operatively, data defining the geometry of the proximal part of the patient's tibia, or distal femur, is collected, for example by carrying out a CT scan. That data is then used in the manufacture of the instrument 100, for example using rapid prototyping techniques, so that the attachment areas of the instrument are adapted to match the surface of the proximal part of the tibia, or distal part of the femur, in a unique way.

Hence, for example, the instrument can be attached to the patient's tibia in only a single unique position. Therefore, in use, the instrument is automatically navigated to the correct position on the patient's tibia, as there is no other position in which the instrument can be reliably attached to the patient's tibia. Once attached, slots 112 and 114 provide a cutting guide which defines a plane along which the tibia can be resected using a suitable cutting instrument or device, such as a saw. The present invention allows that plane to be adjusted, if required, in order to provide soft tissue balancing of the patient's knee.

In each of the embodiments, the gap between the bone surface and the parts of the instrument which are not in contact with the patient's bone, are planned to provide sufficiently clearance from the bone surface to allow +/−3 mm of anterior-posterior or proximal-distal movement and +/−3° of varus-valgus and flexion-extension and interior-exterior rotation. This planning of the shape of the instrument can be achieved by using a grid search of the allowable range of angles and positions in steps of 1 mm & 1° or divisions thereof. Giving in this example 5*5*5*5*5 corresponding to 3124 grid points. For each grid point, constructive solid geometry of operation of the CT scan of the bone against the potential inner instrument surface is carried out. From this, an inner surface of the instrument can be designed and manufactured that will clear any bone, for any desired offset. The unique attachment areas are then placed where they should be for a zero off-set 0,0,0,0,0 position.

As illustrated in FIG. 1, instrument 100 includes an adjustment mechanism, involving the groups of holes 1116 and 118, by which the position of the cutting guide, defined by slots 112 and 114, can be adjusted. When the instrument is first attached to the tibia, pins 120, 122 can be introduced via holes 116, 118 into the tibia. If it is determined that the position of the cut needs to be translated, in order to improve soft tissue balancing, then the instrument can be removed from the femur and then reattached with pins 120, 122 engaged in different ones of the groups of holes 116, 118. In order to do so, it may be necessary to break away a part, or parts, of the instrument. The instrument can include parts which have been engineered to allow them to be easily broken off, for example by introducing a break line or similar.

The use of pins allows the repositioning of all of the cuts in the anterior-posterior and/or proximal-distal directions. The sets of holes 116, 118 are provided with preselected separations, e.g., one millimeter intervals providing up to three millimeters of displacement.

The attachment pins are first inserted into the bone with the instrument in the zero off-set position. When adjustments are required, then the instrument is removed from the bone and replaced with the pins going through the holes that give the required position and angular deviation, any with any changes in the attachment areas as described below. For an easier identification of the correct initial pin holes, the pin holes which are only needed for adjustment can be initially sealed.

For example, in order to accommodate variation in the anterior-posterior position of the cut, the surgeon breaks off the attachment regions on the bone so that the instrument's position can be translated. For example, if the template is to be moved more anteriorly, then the contact points on the posterior side are broken off so that the alignment holes that allow the interior movement can be used. The attachment regions are selected either to allow rotation about the axis of the femur, or so that they can be tracked with certain angles to allow movement in the proximal-distal direction.

This solution is particularly useful as the majority of the force from sawing is transferred from the saw to the bone through the inserted alignment pins 120, 122.

Hence, the embodiments shown in FIG. 1 allows joints that are not balanced in flexion and extension, in the hard-tissue-based pre-planning of the implant position and orientation, to be balanced by re-positioning the implant which can reduce the amount of ligament tissue that is to be released.

The instrument 100 can be made from any suitable material, such as a biocompatible nylon material.

The securing pins and screws can go though a patient specific attachment contact area on the bone, this reduces the stress compared to that which would occur if the pins went through an area of the instrument that was not in contact with the bone.

FIGS. 2A to 2E show perspective views a further version of an instrument 100' corresponding to the first embodiment of the invention in use with a distal end of a femur 102. The instrument 100' has a main body 104' including four slots 123, 124, 125, 126 which provide cutting guides for making an end cut, an anterior cut and posterior condylar cuts of the femur 102 respectively. The instrument 100' has seven members, e.g. 127, each having a free end and which define a plurality of attachment areas. The members are removably attached to the body, e.g. by being break away members or by being attached using a push fit, press fit or similar mechanism. A first arm 128 extends from a first side of the body and a second arm 129 extends from a second side of the body. A portion of the inwardly facing surface of the free end of each arm 128, 129 defines a further attachment area. Each arm 128, 129 is engineered to break away adjacent the body by including a thin portion.

A pair of pyramidal or tapered shaped members 810, 812 extend away from an inner bone facing surface of the body. Each member presents a substantially flat face to the bone surface and tapers toward the body of the instrument to which they are attached in a shallow trench or recess 814 in its surface. The members 810, 812 help to maintain the correct distal resection when the cutting block 100' is translated in the anterior direction.

The cutting block will define the amount of distal resection from the contact position of the end faces of the pyramidal members with the distal femur. As the end of the femur is essentially spherical, and a point contact were used, then when translate the block is translated in an anterior direction the distal resection level would change. By having the members in the gap between the end of the femur and the instrument body with a flat plane end face configured and positioned to pick up and engage the most distal part of each condyle, when the cutting block is translated in the anterior direction by snapping off the other attachments, the cutting block still picks up the most distal part of the femur and maintains the same distal cut. In other words only the anterior-posterior cuts are adjusted to balance the flexion gap. Having the ends surfaces of the members 810, 812 match the surface shape of the femur does not work as the end faces of the members and the condylar surfaces would clash when the cutting block is moved anteriorly. The members 810, 812 stand proud of the inner bone facing surface of the cutting block so that the distal resection can be adjusted, if needs be, by snapping the members 810, 812 off.

In another embodiment, not shown, each member 810, 812 are provided in the form of a plurality of spaced apart parallel ribs of the same generally triangular shape and the free ends of the ribs co-operate to define a generally flat end plane for engaging the condyles.

Figure 2A:
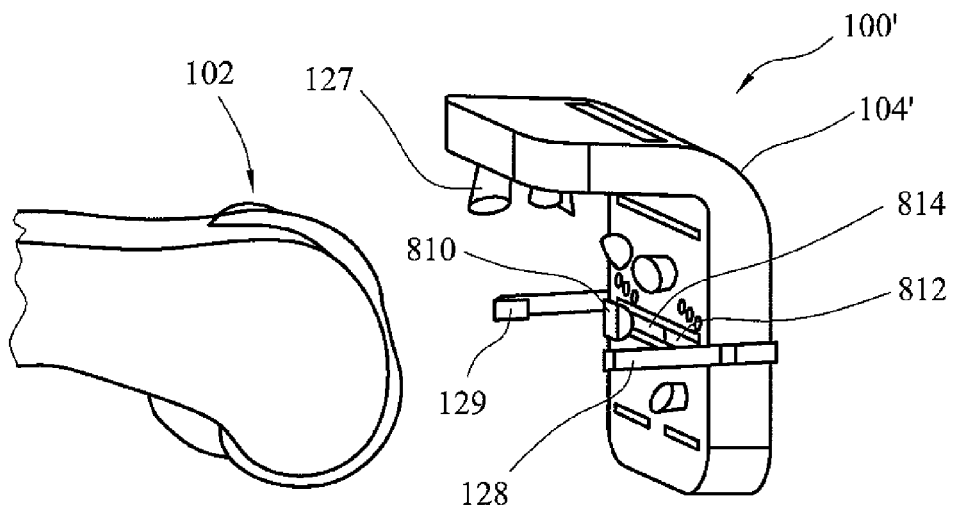
FIGS. 2A to 2E show perspective views of a further embodiment of an instrument according to the invention.
Figure 2B:
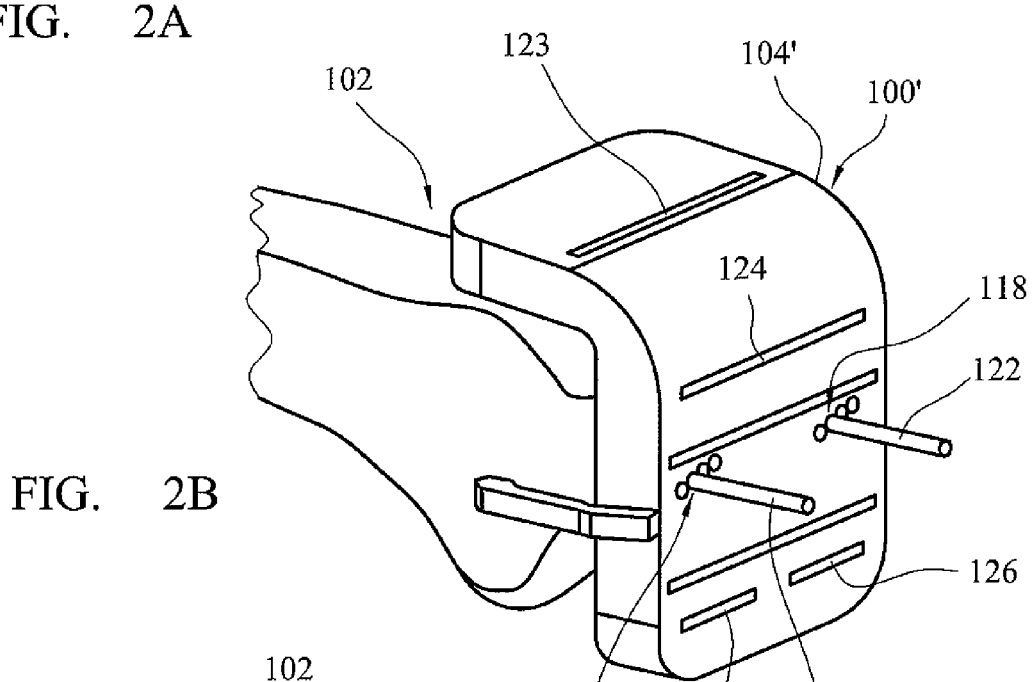
Figure 2C:
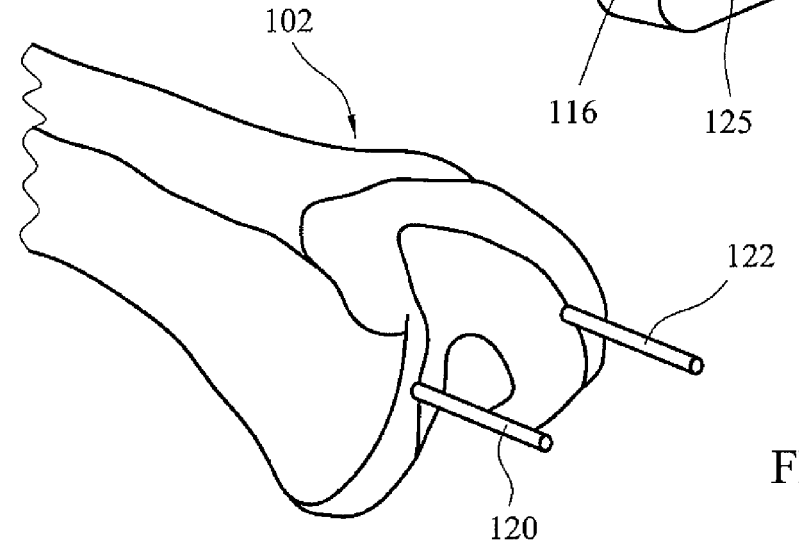
Figure 2D:
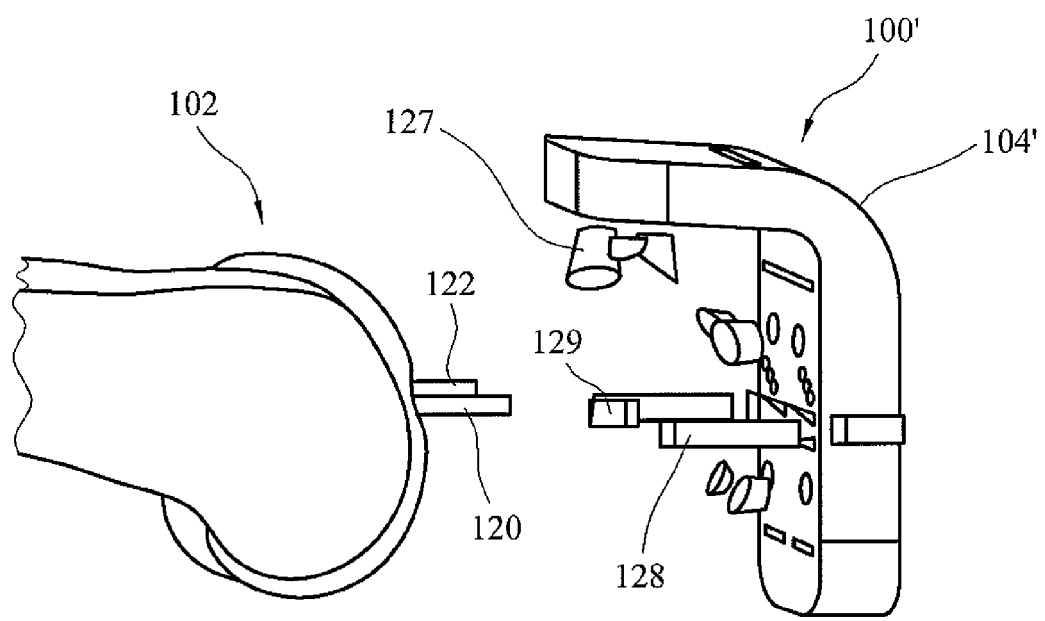
Figure 2E:
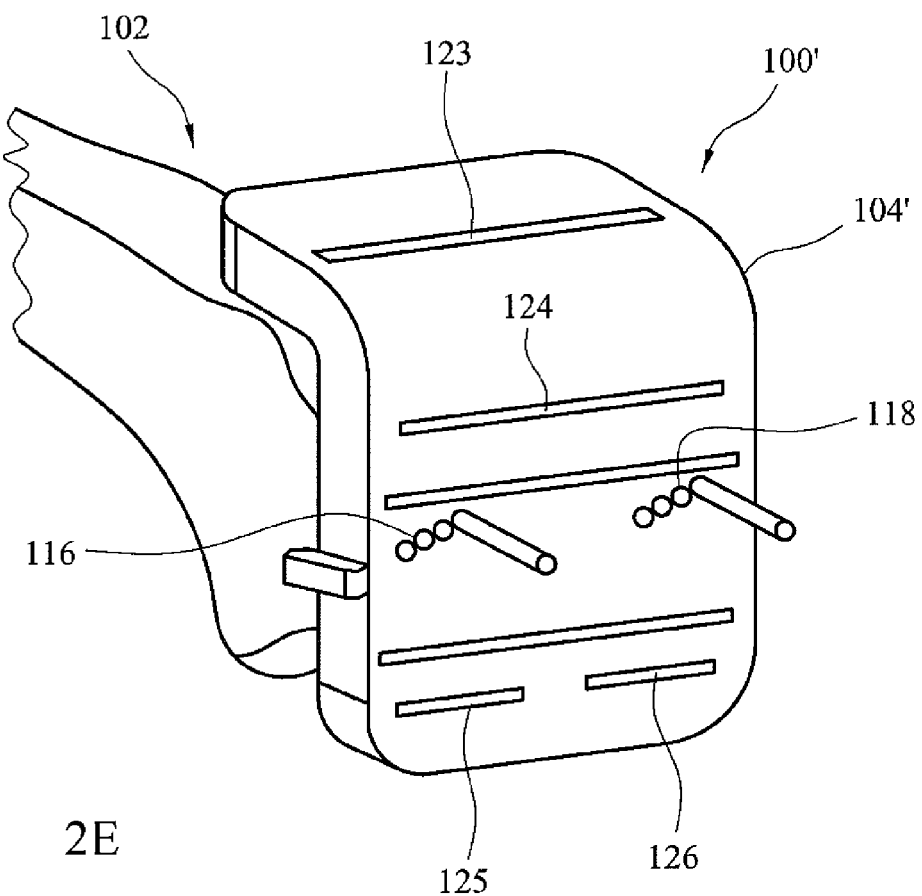

In use, the instrument 100' is presented to the free end of the bone 102, as illustrated in FIG. 2A and then mounted on the bone, as illustrated in FIG. 2B, with the attachment surfaces defining a unique position on the patient's bone at which the instrument 102' can be attached. Bone pins 120, 122 are then introduced via a one of the two groups of pin holes 116, 118 so as to fix the instrument to the bone and determine its initial position. The instrument can then be removed from the bone, as illustrated in FIG. 2C and then the bone engagement members having the attachment surfaces 127 can be detached from the body and the side arms 128, 129 can be broken away from the body, as illustrated in FIG. 2D. The instrument 100' can then be re-attached to the body, as illustrated in FIG. 2E, but with the cutting guides 123, 124, 125, 126 at different positions relative to the initial positions by engaging the bone pins 120, 122 with different ones of the two groups of pin holes 116, 118 so as to reposition the cuts compared to the initial positioning of the instrument 100'.

Figure 3:
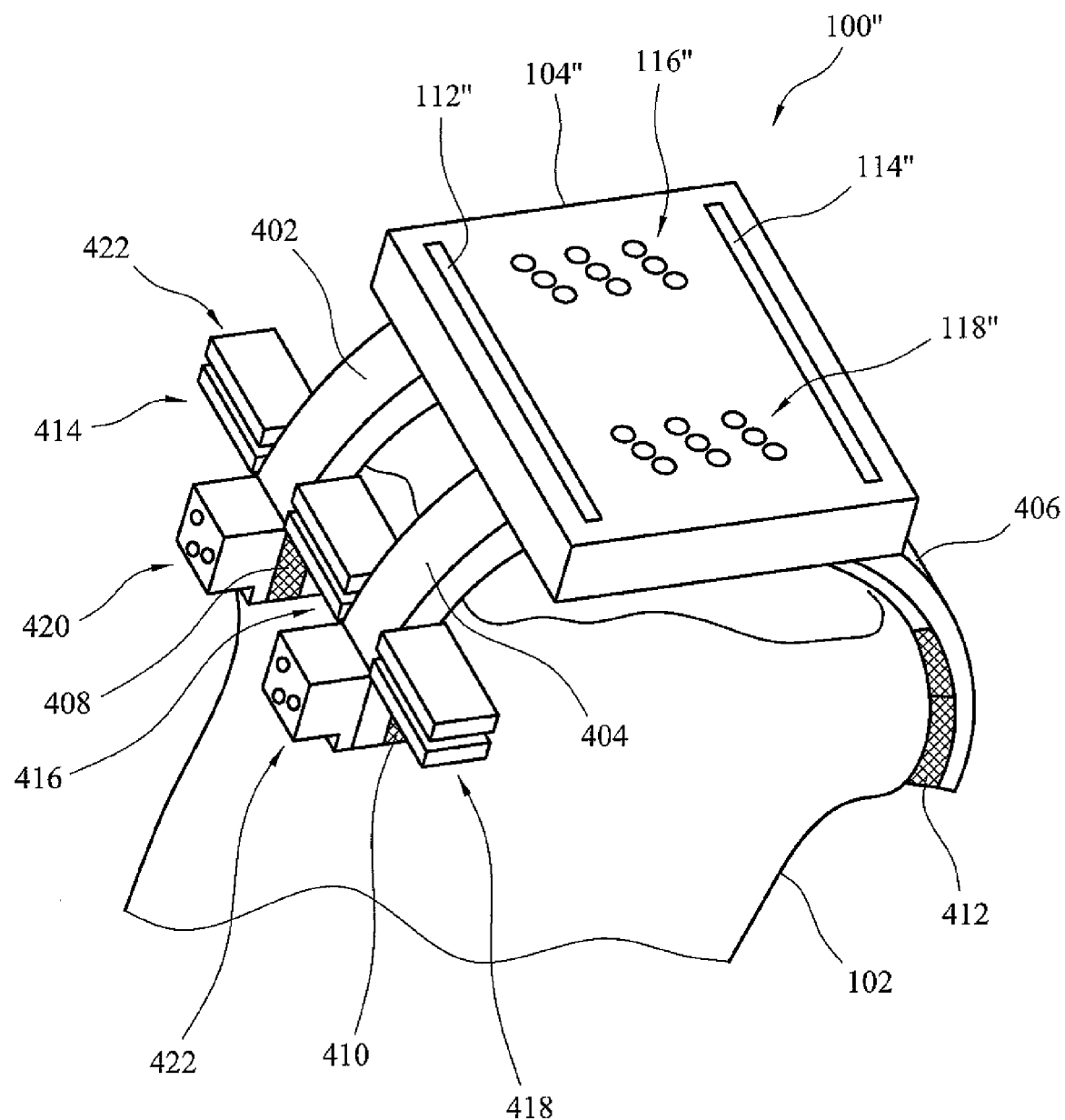
FIG. 3 shows a perspective view of a further embodiment of an instrument according to the invention.

FIG. 3 shows a perspective view of a further version of an instrument 100" corresponding to the first embodiment of the invention in use with a distal end of a femur 102. Instrument 100" has a main body 104" bearing a first and a second slot 112", 114" which provide cutting guides for making anterior and posterior cuts. A pair of leg members, e.g. legs 402, 404, extend from an anterior side and a posterior side of the body 104" (although only one of the second pair of legs 406 can be seen in FIG. 3). Toward a free end of each leg, an attachment area is provided by an inward facing surface of a pad of material 408, 410, 412. A third cutting guide 412 is provided by a slot defined by and extending over three pairs 414, 416, 418 of spaced apart plates, with the spacing between the plates defining the slot. The pairs of plate are attached to and supported by and between the legs 402, 404. A first group of nine apertures 116" and a second group of nine apertures 118" are provided in the body for receiving bone pins 120, 122 in use. A third group of three apertures 420 and a fourth group of three apertures 422 are provided in feet portions of the legs and toward the free ends of the legs. Corresponding registered apertures are also provided in the pads of material 408, 410 located behind the feet, so that bone pins can pass through the apertures and pads and into the bone 102". As mentioned above, providing the attachment mechanism at the same position as the bone attachment areas helps to reduce stresses during use of the instrument as a cutting guide.

Use of the instrument 100" is similar to that described above and the legs are broken off, disconnected or otherwise removed from the main body 104 between initial attachment and re-attachment of the instrument to allow posterior-anterior or internal/external rotation. In other embodiments, the legs are not removed and the contact pads 408, 410, 412 are deformable or removable so as to adjust the block. In another embodiment one or more of the legs can be bent away from the bone in order to adjust the position of the cutting block. A first subset of the first group 116" of holes and a first subset of the second group of holes 118" allow adjustment of the instruments position in the anterior-posterior direction. A second subset of the first group of holes 116" and a second subset of the second group of holes 118" allows adjustment of the internal-external rotation of the femur. When this type of rotation is required, then new pins are placed in the central rotating holes and the cutting guide is re-positioned using the appropriate rotating pin holes. The top row of holes provides negative rotation angles for various anterior-posterior positions, the middle rows of holes provide pure anterior-posterior displacement and the bottom row of holes provide anterior-posterior displacement with positive rotation angles. Some of the holes allow adjustment of the position of the instrument in both directions. Hence adjustment of the instruments position in either or both directions is possible. The diagonal offset of the holes allow 6 mm pins to have less than 6 mm adjustment (e.g. typically 2 mm of adjustment) without having the holes overlap. Pairs of holes are positioned generally parallel to the slot. That is a line between a hole in the first group 116" and the corresponding hole in the second group 118" will be parallel to slot 114". A more complicated hole pattern can be used with holes positioned on an arc to allow rotation to be adjusted as well as the anterior-posterior position by replacing the block so the pins go through a hole on the middle row and one on the top or bottom row on the other side.

The third group of holes 420, and fourth group of holes 422 allow adjustment of the instruments position in the proximal-distal direction and varus-valgus angle of the distal cut. The holes in the third and fourth groups are arranged in a generally triangular pattern so that the holes can be placed closer together in the proximal-distal direction, so that a bone pin of a certain size, e.g. 3 mm diameter, can provide adjustment in smaller, e.g., 2 mm, steps, by displacing the holes from side to side.

Figure 4:
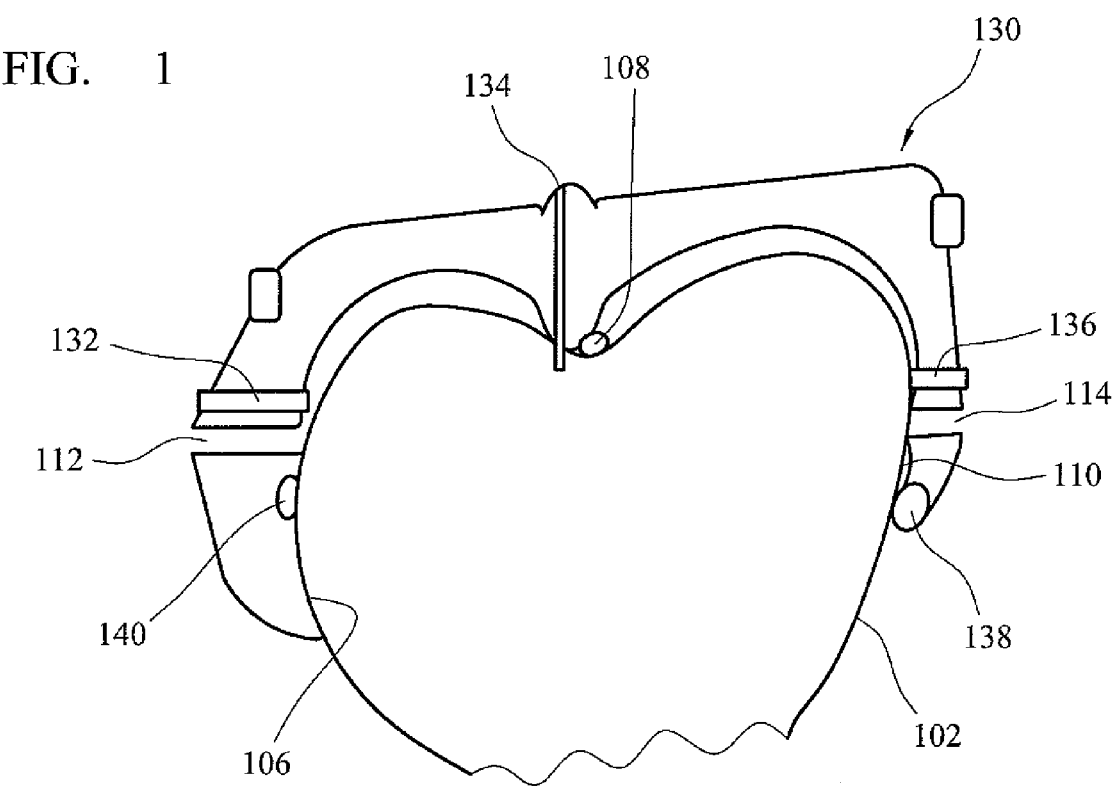
FIG. 4 shows a schematic cross sectional view through a second embodiment of a surgical instrument according to the invention.

FIG. 4 shows a cross-section through a second instrument 130 illustrating a second embodiment of the invention. Instrument 130 is similar to instrument 100. However, instrument 130 includes a different adjustment mechanism by which the position of the cutting guide defined by slots 112, 114 can be adjusted. Instrument 130 includes first 132, second 134 and third 136 crumple zones by which the shape of the instrument can be deformed. The crumple zones 132, 134, 136 can be provided by any suitable engineering construct, such as an area made of a different material or an area with a specifically engineered weakness. For example, the crumple zone can be provided by a wafer type structure. Shims and wedges can be inserted into crumple zones that are not to be crumpled, to ensure that only the correct zones crumple when a crumple zone compressing force is exerted on the instrument.

In use, after the instrument 130 has been attached to the distal end of the tibia 102, if measurements indicate that the position of the cut should be changed in order to provide soft tissue balancing, then the surgeon can manipulate the instrument 130 to deform its shape thereby changing the position or orientation of slots 112, 114 while the instrument 130 is still attached to the femur. Hence, the multiple attachment points, which are uniquely configured to the shape of the patient's bone, ensure that the instrument is reliably navigated to the correct position on the patient's bone and the crumple zones provide a mechanism by which the position or angle of the cut or cuts can be adjusted to allow a cut or cuts appropriate to the soft tissue balancing required to be made. With crumple zones in an anterior-posterior direction with respect to the attachment pins it is possible to move the cuts in the anterior-posterior direction or interior-exterior. Wedges can be used to fill the space left by movement of the pins. For a single planar cut, e.g. on a tibia, planar crumple zones above the cut can give proximal and angular variation.

Figure 5:
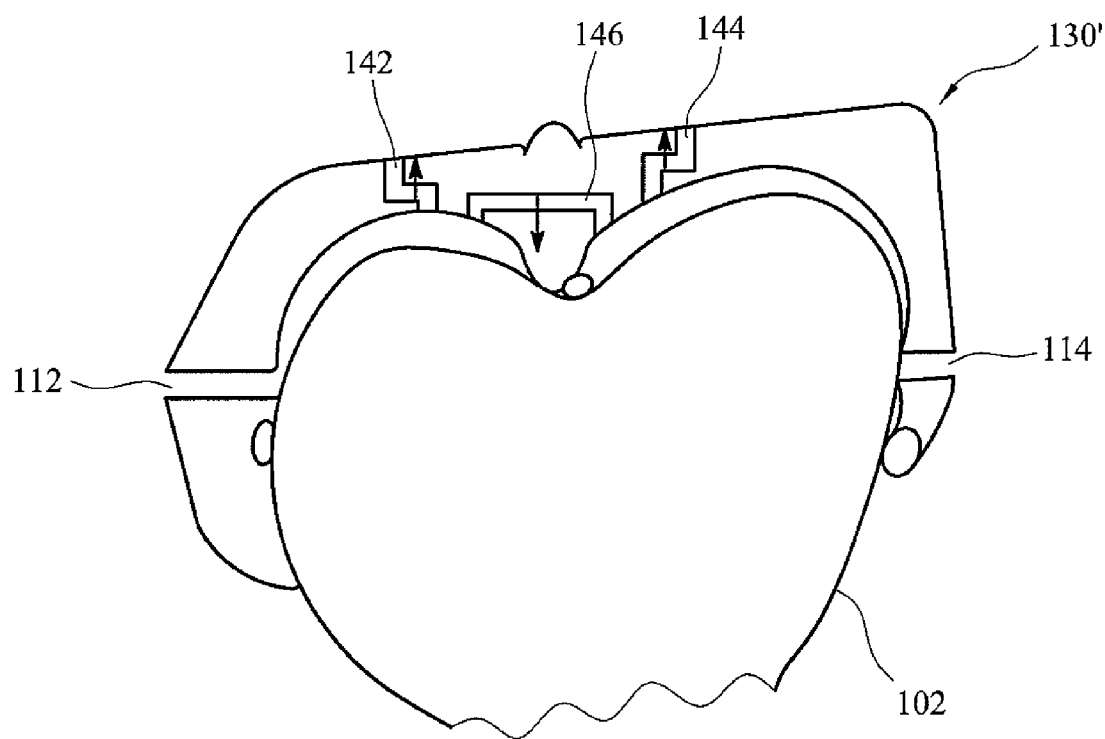
FIG. 5 shows a schematic cross sectional view through a further version of the second embodiment shown in FIG. 4.

FIG. 5 shows a further embodiment 130' of the invention similar to that shown in FIG. 4. In this multi-cut instrument 130' the crumple zones 142, 144, 146 are in the form of a trench about the attachment pins and allow the whole cutting block to be moved away from or toward the bone. For example, as illustrated in FIG. 5, compressing the first crumple zone 146 will move the cuts further into the bone, in the direction indicated by the associated arrow in FIG. 5. Whereas, compressing the second pair of crumple zones 142, 144 will move the cuts further out of the bone, in the direction indicated by the associated arrows in FIG. 5.

The crumple zones allow the position and angle of all the cuts to be adjusted.

Additionally, the instrument can include small spacers 138, 140 which can be attached to various points on the interior of the attachment areas of the instrument to provide further changes in position or angle. Small holes (not shown) or attachment points in the instrument are provided into which these spacers can be mounted using a push-fit mechanism.

Figure 6:
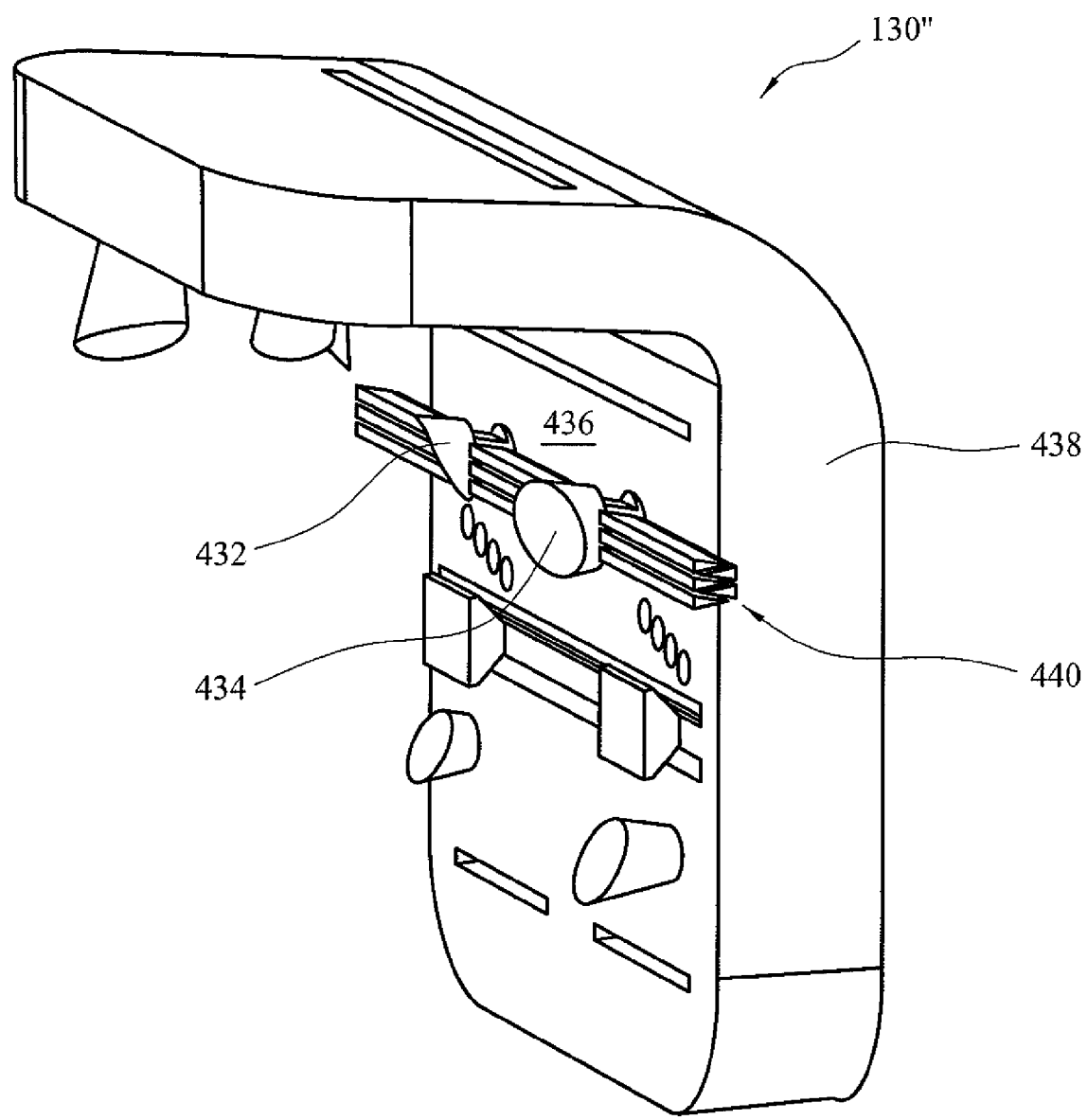
FIG. 6 shows a perspective view of a further embodiment of an instrument according to the invention.
Figure 7:
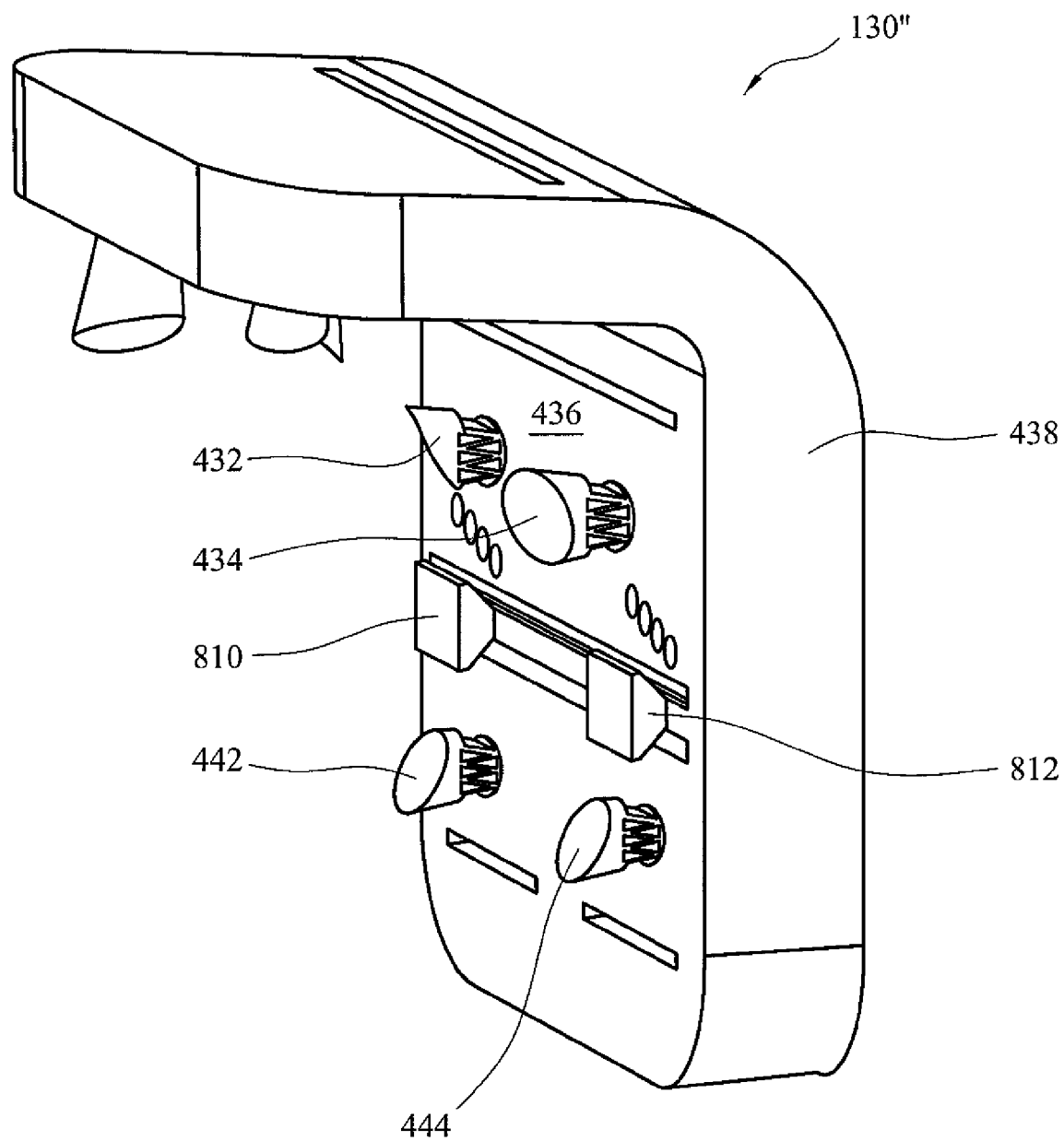
FIG. 7 shows a perspective view of a further embodiment of an instrument according to the invention similar to that shown in FIG. 6.

FIGS. 6 and 7 show perspective views of a further version of an instrument 130" according to the second embodiment of the invention and which uses crumple zones. The instrument is generally similar to that shown in FIGS. 2A to 2E, but rather than having break away or removable parts, crumple zones are used to allow the position of the cutting guides to be adjusted. Two 432, 434 of the members extending from an inner, bone facing surface 436 of the body 438 of the instrument have generally triangular shaped voids passing through them, between the bone engaging attachment area surface and the point at which the members 432, 434 are attached to the inner surface 436. Removable support members in the form of triangular shaped wedges 440 are located in, and are removable from, the voids, are shown in FIG. 6 so that the members are correctly positioned for initial attachment of the instrument 130" to the patient's bone. The support members are individually removable so that the amount and/or direction of deformation of the members can be selected by the user of the instrument, depending on which of the support members are removed.

After attachment to the patient's bone, some or all of the wedges are removed from the voids and the instrument can be manipulated so that the members 432, 434 deform thereby allowing the cutting guides to take up a different position relative to the bone. FIG. 7 shows an instrument similar to that shown in FIG. 6, in which the wedges have been removed and in which a further two of the members 442, 444 have been provided with voids defining crumple zones by which the members can be deformed. Crumpling members 432, 434, 442 and 444 will give a change in the proximal-distal direction. The provision of crumple zones in a perpendicular direction can be used to adjust the anterior-posterior position.

The instrument can be adjusted similarly to the method described above and with the deformable members deforming out of the way. Alternatively, the instrument can be adjusted prior to pinning the instrument to the bone. The method would then be to place the instrument on the bone in its initial position, remove the wedges, adjust the position of the instrument as required by deforming the members, pin the cutting block in the adjusted position and then make the adjusted cut. In another embodiment, deformable members are also used under the anterior flange of the instrument.

Figure 8:
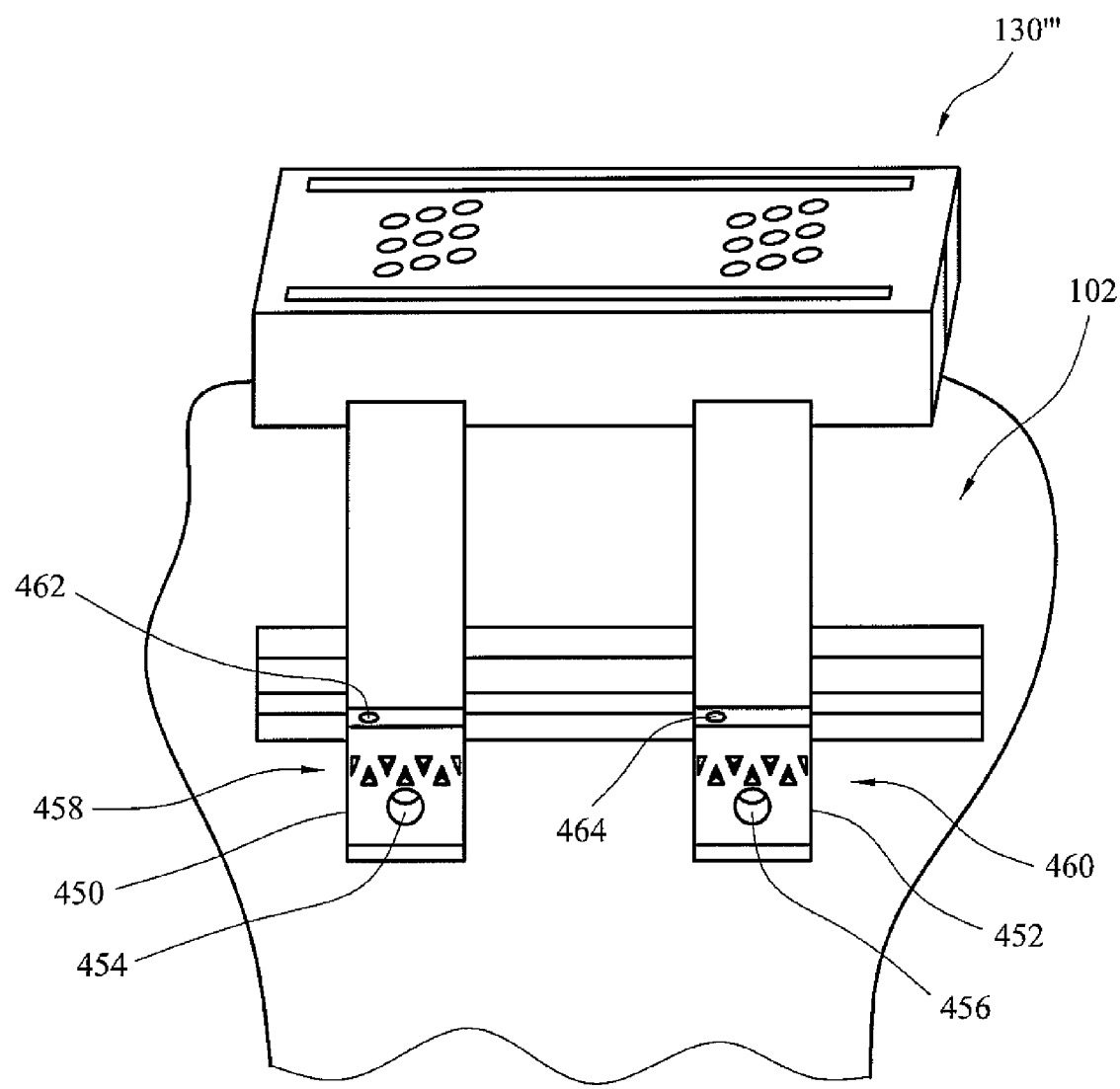
FIG. 8 shows a perspective view of a further embodiment of an instrument according to the invention.

FIG. 8 shows a further version of an instrument 130'" according to the second embodiment of the invention which includes crumple zones. The instrument is generally similar to instrument 100" shown in FIG. 3. However, each foot 450, 452 includes a single aperture 454, 456 by which the instrument can be pinned to the bone 102 in use. A portion of the foot above the aperture has a plurality of triangular apertures passing therethrough, providing a crumple zone 458, 460 by which the position of the instrument in the inferior-superior direction can be adjusted. Above each crumple zones an aperture 462, 464 is provided for receiving a threaded fastener (not shown) which is received in a treaded aperture below the crumple zone so that by operating the threaded fastener the top and bottom parts of the crumple zone are urged together so as to crush the supporting structure and hold the crumple zone in a preferred degree of deformation. This can be particularly useful, if the crumple zone material is resilient and so the threaded fastener can be operated to crush or release the crumple zone with the instrument changing its position accordingly.

Figure 9:
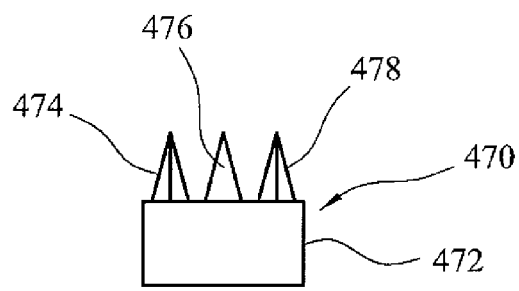
FIG. 9 shows a schematic side view of a removable support member which can be used with the instrument shown in FIG. 8.

FIG. 9 shows a removable support part which can be used with various of the second embodiments. The support part 470 has a body 472 with a plurality of wedges 474, 476, 478, three in the illustrated embodiment, extending form a side thereof and sized and shaped to be receivable in the triangular apertures of the crumple zones 458, 460. The wedges can be pushed into the apertures in the crumple zones to prevent them collapsing when the instrument 130'" is being initially mounted on the bone and then removed when it is desired to change the position of the instrument by deforming the crumple zones.

The wedges can also be used when the crumple zones have been partially collapsed, by forcing them into the apertures so that the apertures in the crumple zones are at least partially reformed and the instrument caused to change its position at least partially back to its initial position.

Figure 5A:
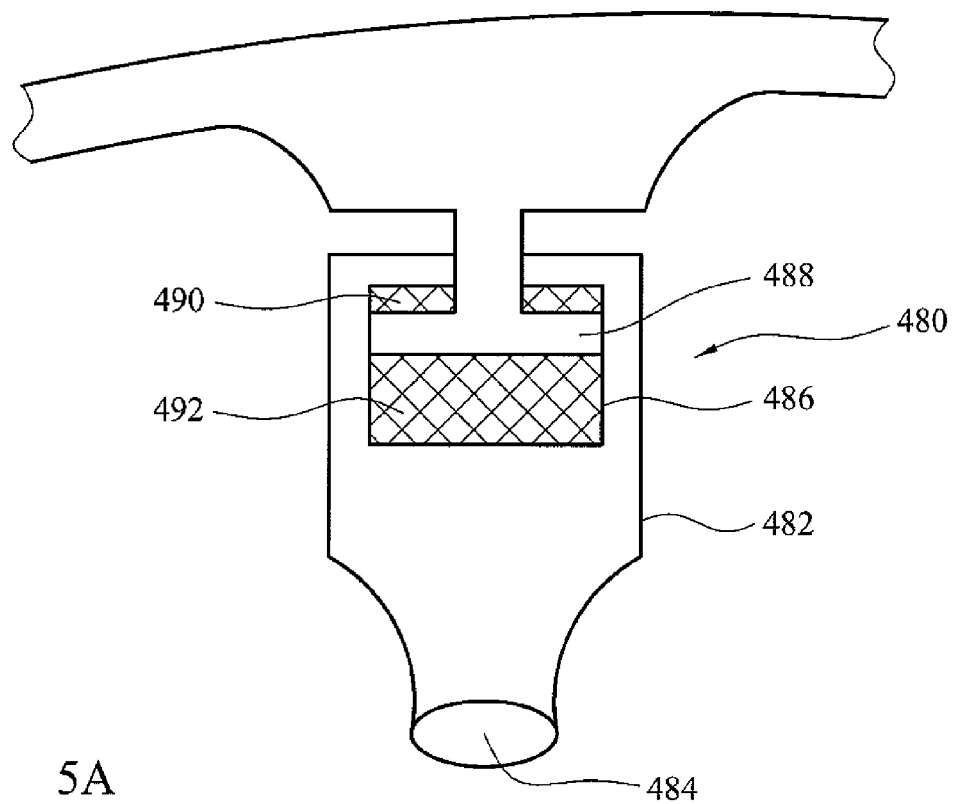
FIG. 5A shows a schematic cross section through an adjustment mechanism part of an instrument according to the invention.

FIG. 5A shows a further crumple zone mechanism 480 that can be used in various embodiments of the invention, such as instrument 130' shown in FIG. 5. The crumple zone mechanism 480 can be used to replace the crumple zone shown in FIG. 5. A part of the instrument 482 including the attachment area 484 has a chamber 486 including material which can be deformed. A foot part 488 of another part of the instrument is slidingly received in the chamber with portions of deformable material above 490 and below 492 the foot part. The position of the instrument can be adjusted toward the bone by compressing and deforming the lower portion of material 492 or the position of the instrument can be adjusted away from the bone by compressing and deforming the upper portion of material 490.

Figure 10:
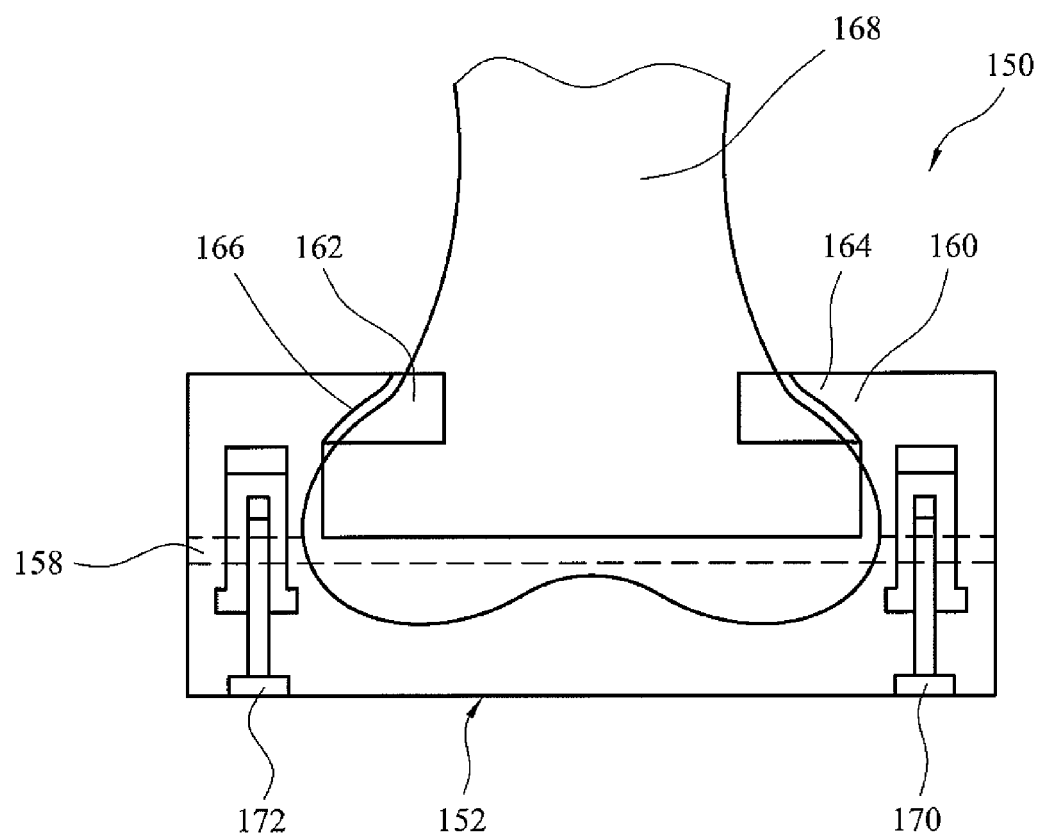
FIGS. 10 and 11 show schematic cross sectional views through a third embodiment of a surgical instrument according to the invention.
Figure 11:
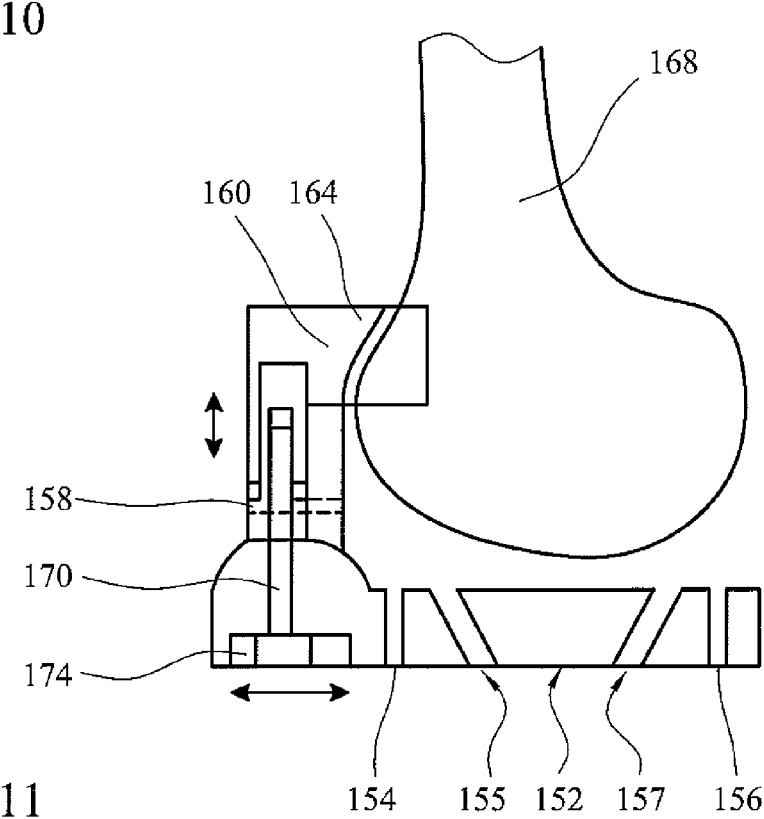

FIGS. 10 and 11 show schematic cross-sections through a third embodiment 150 of the invention in the coronal and sagittal plane, respectively. The third embodiment of the instrument 150 includes a main body section 152 which bears first 154, second 156 and third 158 slots which provide three cutting guides for receiving a cutting instrument, such as a saw, in use. In other embodiments, further cutting guides can also be provided, e.g. 155 & 157. Instrument 150 includes a first member 160 having a first attachment area 164 having a surface shape matching the shape of the surface of a corresponding region of the patient's bone. A second member 162 also has an attachment area 166 having a surface shape matching the shape of a corresponding area of the surface of the patient's bone 168. Further attachment members providing further attachment areas in the same plane or out of the plane of the attachment areas 162, 164 can also be provided. As illustrated in FIG. 10, the bone 160 is a distal femur showing in the lateral plane. However, the same principles can also be applied to the tibia.

The first attachment member 160 includes a first screw mechanism 170. The second attachment member 162 includes a second screw mechanism 172. Screw mechanisms 172 or 170 can be operated to translate the cutting guide 158 relative to the bone 168 in a proximal-distal direction, as illustrated by the double headed arrows shown in FIG. 11.

The instrument 150 includes a further adjustment mechanism 174, in the form of a long hole, by which the screw mechanism 170 can be moved with respect to the body 152 in an anterior-posterior direction as illustrated by the associated double headed arrow in FIG. 11. A second, similar adjustment mechanism (not shown) is provided for the second screw mechanism 172. The adjustment mechanisms 174 are operable to translate the main body 152 in an anterior-posterior direction so as to move the position of the cutting guide anteriorly or posteriorly relative to bone 168. The screws themselves can be of captive-pane type or similar with a threaded bushing inside the block, in order to prevent interference of the top or the end of the screws with the body tissues. Varus-valgus variation of the cutting plane can also be achieved by alternative settings of screws 170 and 172.

Hence, as the shapes of the attachment areas 162, 164 are specific to the patient's bone, there is a unique position on the patient's bone at which the instrument can initially be place on the bone. Once the instrument is pinned in place, or prior to pinning, the position of the cutting guides 154, 156, 158 can be adjusted by using the screw mechanisms to move body 152 to allow the positions of the anterior, posterior and distal cuts to be adjusted. Attachment is also provided by pins that pass through the attachment members 162, 160 and the surface matching areas, on the anterior side of the bone, in positions that are central to the anterior face. As will be appreciated, in this embodiment, the screw mechanisms provide the adjustment mechanism. Colours or other indicia or markings can be provided on the screws to allow the position to be altered or adjusted by predetermined amounts. The amounts to be used can be specified in a look up table or from a computer program that have been derived from soft-tissue balancing measurements.

Figure 12:
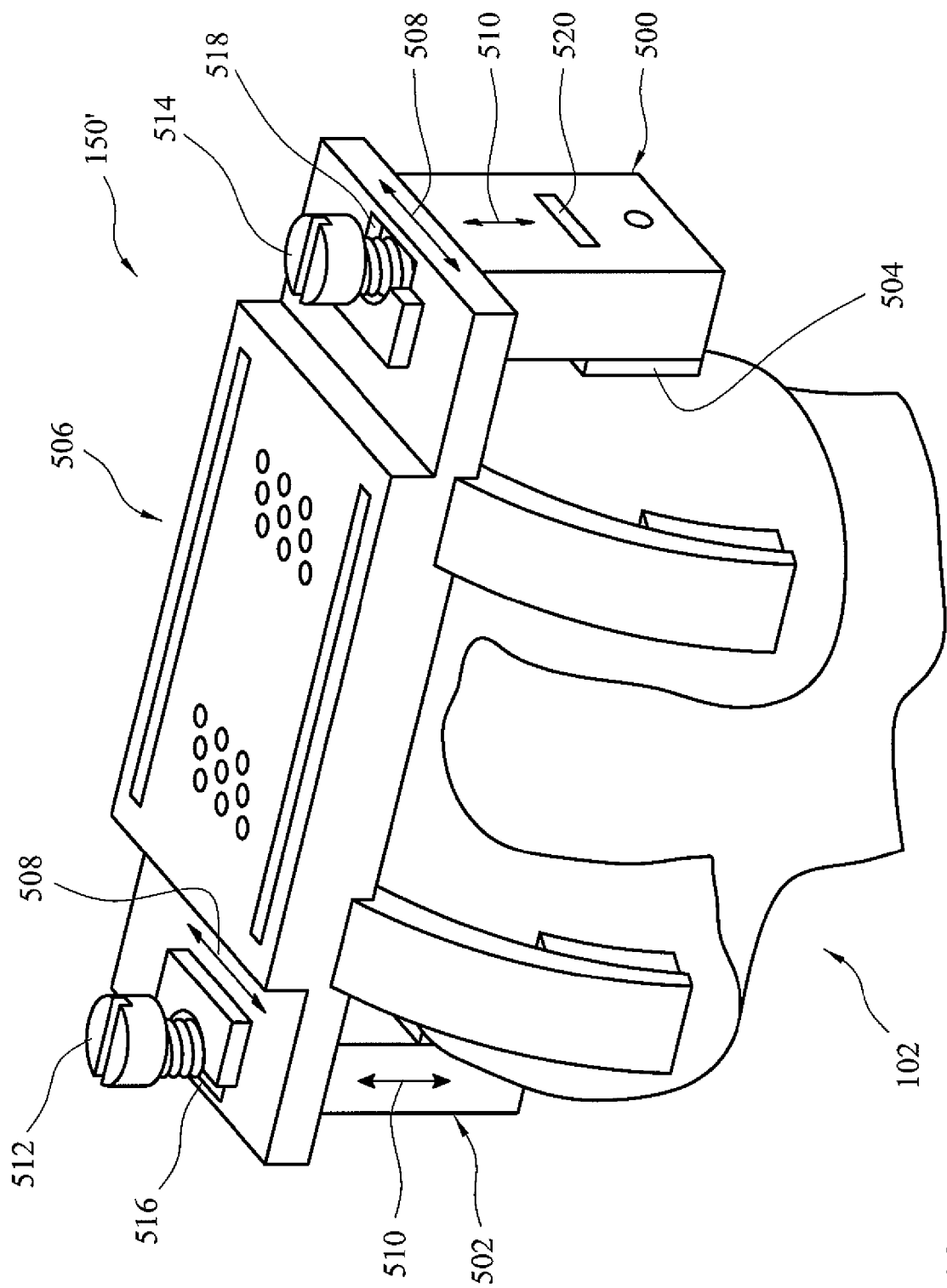
FIG. 12 shows a perspective view of a further embodiment of an instrument according to the invention.

FIG. 12 shows a further version of an instrument 150' according to the third embodiment of the invention. Some of the features of the instrument 150' are similar to those of the instruments shown in FIGS. 3 and 8 and so are not described again in detail. However, the mechanism for adjusting the position of the instrument differs. A patient specific foot 500, 502 is provided at each end of the instrument body and includes a surface providing an attachment area 504. Each patient specific foot is attached to the main body 506 by an adjustment mechanism which allows movement of the body 506 relative to each foot independently in the anterior-posterior direction 508 and/or in the inferior-superior or proximal-distal direction 510.

Each adjustment mechanism uses a captured screw 512, 514 which passes through a threaded plate 516, 518 which can slide in a plate receiving formation in the anterior-posterior direction 508. A capture plate 520 is provided in each block to hold the block 500, 502 at a fixed position with respect to the end of its screw. A feature on the underside of the body interacts with a mating feature on the block to prevent rotation of the block 500, 502 relative to the body 506. The screws 512, 514 can be rotated to cause the body 506 to move in the proximal-distal direction relative to the bone an so adjust the position of the cutting guides after the instrument 150' has been mounted on the bone 102.

Figure 13:
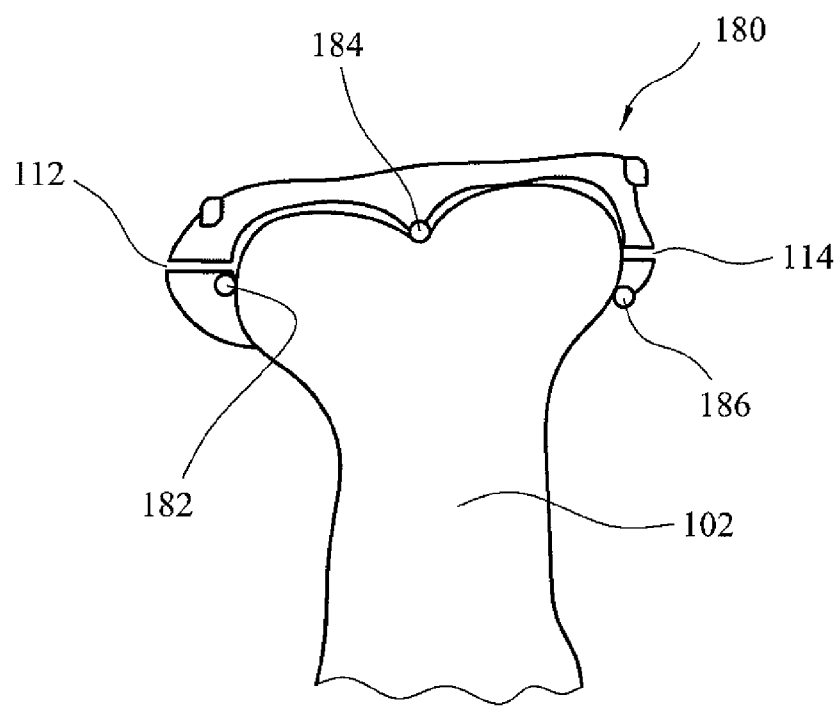
FIG. 13 shows a schematic cross sectional view through a fourth embodiment of a surgical instrument according to the invention.

FIG. 13 shows a schematic cross-section through a fourth embodiment 180 of the instrument. The fourth embodiment is similar to the first and second embodiments. However, the adjustment mechanism is provided in the form of individual spacers 182, 184, 186 that can be selectively attached to the attachment areas so as to adjust the position of the cutting guide, defined by slots 112 and 114, relative to the bone 102. The individual pieces can be attached using a push-fit or snap-fit mechanism and can be made of a plastics material. The spacers can be colour coded to indicate what change in the position of the cutting guide will result when using the particular spacer. The spacers can be made to fit behind the surface matching areas or on top of them or can replace the surface matching areas patch completely in different embodiments.

Figure 14A:
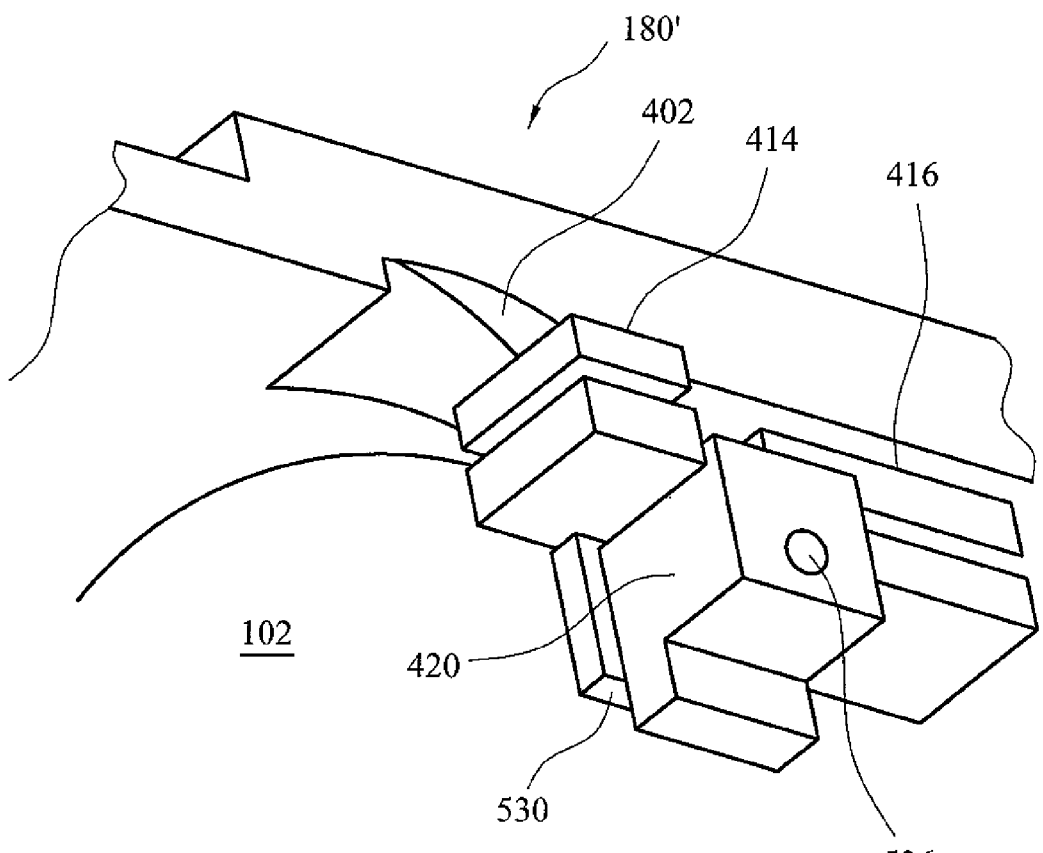

FIG. 14A shows a perspective view of a part of a further version of an instrument 180' according to the fourth embodiment of the invention which uses patient specific spacers. The instrument 180' is generally similar to those shown in FIGS. 3, 8 and 12. Rather than having pads providing the attachment areas, spacers and patient specific contact areas are used to mount the feet portions 420 of the instrument to the patient's bone 102. For example, FIG. 14B shows a patient specific component 530 a bone facing surface of which 532 is shaped to match the shape of the patient's bone and provides an attachment area. An upper surface of the component has a generally tray like form and ends of the tray are sized and configured to provide a push fit attachment to the foot of the instrument 420 as best illustrated in FIG. 14A. An aperture 534 is provided in the body of the tray and in registration an aperture 536 in the foot of the instrument for receiving a bone pin passing through the foot so as to attach the instrument to the bone 102.

FIG. 14C shows a further push fit component 540 which also has a bone facing surface of which 542 is shaped to match the shape of the patient's bone and provided an attachment area. This component 540 has two apertures 544, 546 so that the component can be attached to the foot 420 at two different discrete positions while allowing a bone pin to pass through the foot and component. Hence, this component allows movement of the instrument in the proximal-distal direction.

FIG. 14D shows a further push fit component 550 which also has a bone facing surface of which 552 is shaped to match the shape of the patient's bone and provided an attachment area. This component 550 has a single extended aperture 554 which is shaped with a plurality of waists so that the component can be attached to the foot 420 at three different discrete positions while allowing a bone pin to pass through the foot and component. Hence, this component allows discrete linear movement of the instrument in the proximal-distal direction but at a fixed angle FIG. 14E shows a spacer component 560 also having a generally tray like shape and sized and configured to form a stacked arrangement with the patient shape specific components illustrated in FIGS. 14B to 14D. An extended aperture 562 is provided in the body of the tray to allow a bone pin to pass through the stacked arrangement in use. This spacer allows for angular and linear displacement of the instrument. FIG. 14F shows a spacer component 570 also having a generally tray like shape and sized and configured to form a stacked arrangement with the patient shape specific components illustrated in FIGS. 14B to 14D. An extended aperture 572 having two waists is provided in the body of the tray to allow a bone pin to pass through the stacked arrangement in use in three discrete positions. This spacer allows only linear displacement of the instrument.

FIG. 14G shows a stacked arrangement 580 of a spacer, e.g. spacer 560, and a patient specific shaped component, e.g. component 550. The spacer is dimensioned and configured to provide a push fit attachment of the arrangement via the spacer to the foot 420. The patient specific shaped component is then push fit attached to the spacer.

In use, the initial position of the instrument is planned with at least one spacer on each side of the bone. Hence, the position of the instrument can be adjusted by using different thickness spacers to move the instrument in the anterior-posterior direction. Additionally, or alternatively, spacers can be moved from one side of the bone to the other which also adjusts the position of the instrument in the anterior-posterior direction.

As shown, the spacers have a constant thickness. However, it is also possible to vary the angular position of the instrument by using spacers which have a varying or tapering thickness.

Figure 15:
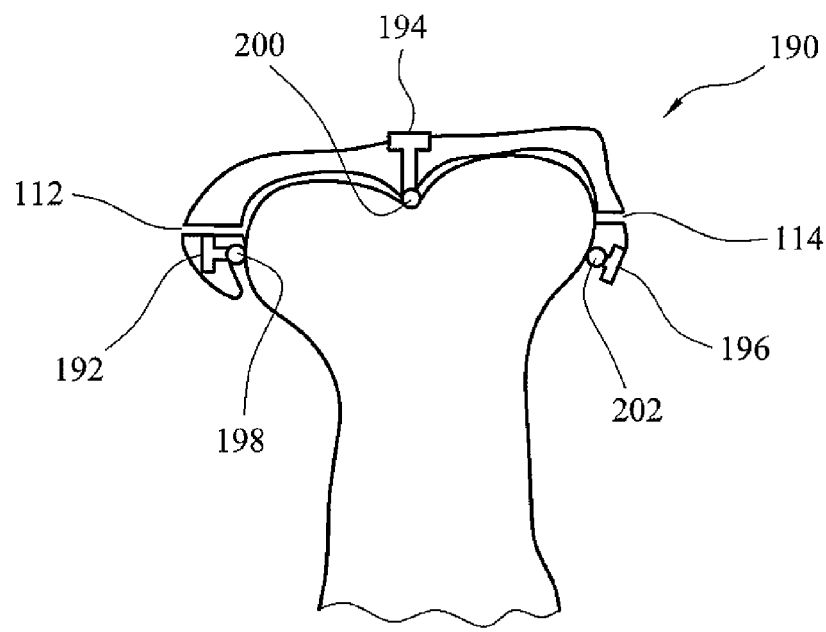
FIG. 15 shows a schematic cross sectional view through a fifth embodiment of a surgical instrument according to the invention.

FIG. 15 shows a schematic cross-section through a fifth embodiment 190 of the instrument. The fifth embodiment is similar to the first, second and third embodiments. However, in the fifth embodiment, the adjustment mechanism is provided by three screws 190, 194, 196 each received in a threaded hole. The foot of each screw bears a member whose outward surface provides an attachment area whose shape substantially matches the shape of the surface of a corresponding region of the patient's bone 102. Hence, the patient specific attachment areas on the feet of the screws 198, 200, 202 allow the instrument to be attached only to a single unique position on the patient's bone, while operating the screws 192, 194, 196 allows the cutting guide, provided by slots 112, 114, to be moved relative to the bone 102. Channels are provided in the main body of the attachment 190 so that the contact feet can slide in the channels and maintain the correct foot orientation, with respect to the local bone surface and the body of the instrument. The angle and position of the screws and channel are optimised to maximise the area of contact to the patient specific part for the expected range of soft tissue dependent angle and position changes. Attachment pins can be placed through a surface matching attachment area to improve the stability of attachment.

Figure 16:
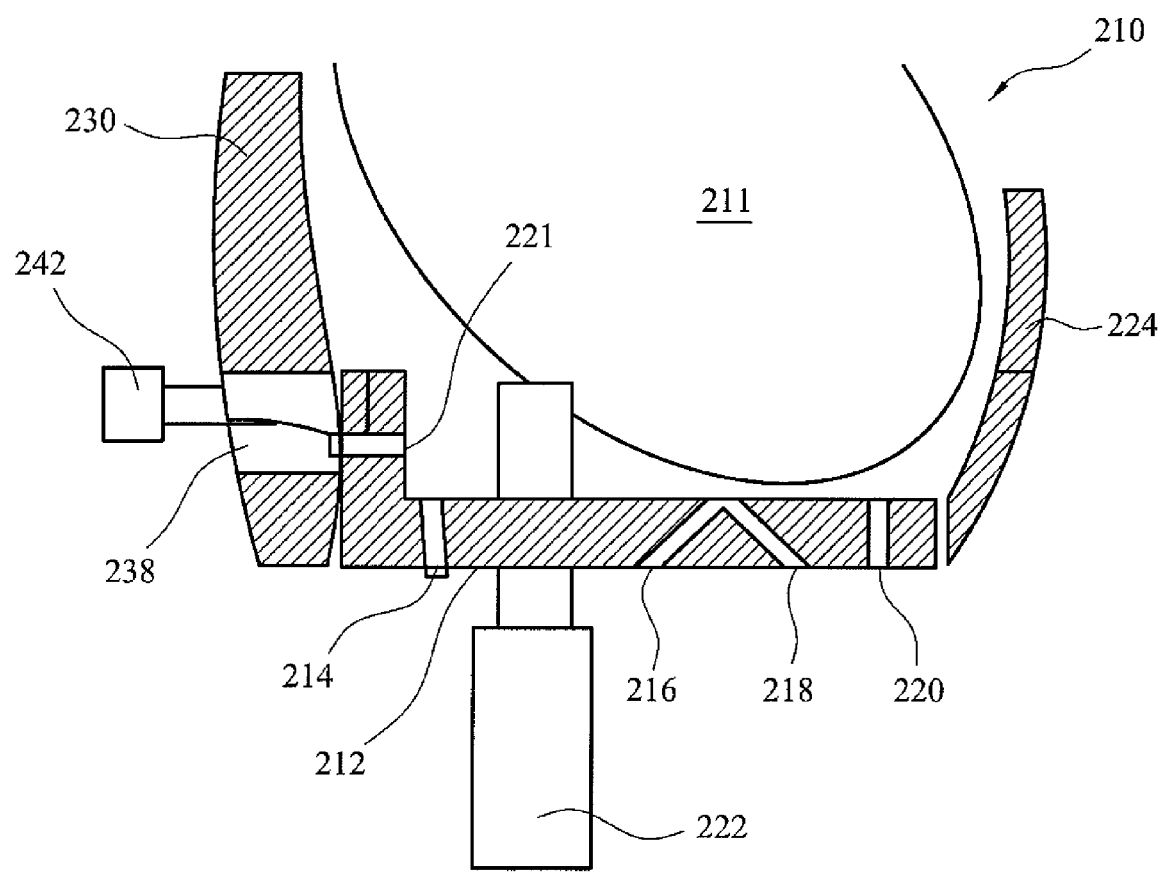
FIGS. 16 and 17 show a perspective views of a sixth embodiment of a surgical instrument according to the invention.
Figure 17:
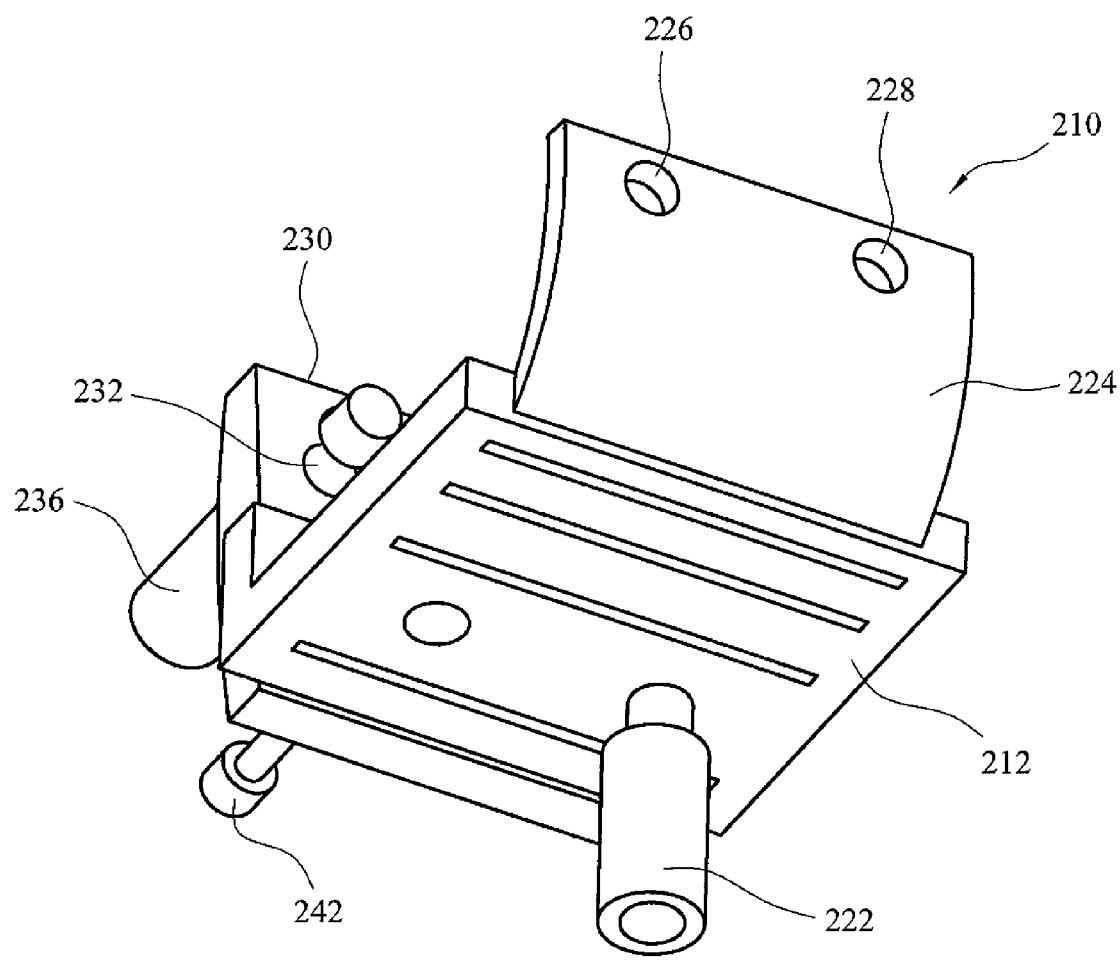

FIG. 16 shows a schematic cross sectional side view of a sixth embodiment 210 of a surgical instrument according to the invention intended for use with the distal end of a femur 211. FIG. 17 shows a perspective view from an underside of the sixth embodiment 210. The instrument 210 includes a main body 212. Body 212 bears a first slot 214, a second slot 216, a third slot 218, a fourth slot 220 and a fifth slot 221. First slot 214 provides a cutting guide for accepting a saw blade for making an anterior femoral cut. Second and third slots 216, 218 respectively provide cutting guides for receiving a saw to make first and second femoral chamfer cuts. Fourth slot 220 provides a further cutting guide allowing a femoral posterior cut to be made. Fifth slot 221 provides a further cutting guide allowing a femoral distal cut to be made.

Body 212 includes two threaded hole each of which can receive a threaded member 222 therein. Other threaded holes in parallel planes behind member 222 can also be provided. A first end of the body 212 includes a first curved end plate 224 having first and second threaded holes 226, 228 therein toward a free end. A second curved plate 230 is provided at a second end of the body 212 and includes a first set of offset threaded holes 232 and a second set of threaded offset holes toward a free end thereof Each of the holes receives a threaded member (not shown) similar to threaded member 222. Hence, in practice, six threaded members are provided and the free ends thereof provide six attachment areas by which the instrument 210 can be attached to the distal end of the femur, or other body in other embodiments. The ends of at least one of screws 222, 236 are shaped to match the shape of the surface of the bone.

The end bone contact areas are keyed with respect to the instrument so they do not rotate when the screws on which they are mounted are rotated. Screw members that are not tipped with surfaces that match the bone surface are tipped with a point, the position of which is known with respect to the surface described by the medical images. In the described embodiment the number of screws used is six, but fewer screws can be used if fewer dimensions are to be changed. For purely positional adjustments this can be reduce to two, e.g., to allow anterior-posterior and proximal-distal changes. In cases where the angles of the cuts are changed there will be a small amount of shear force on screws with surface matching areas. For small angular changes (<3°) that are allowed for, this will not affect the surface match and will be absorbed in the mechanism part-to-part interfaces.

Second end plate 230 includes a slot 238 toward a lower end thereof providing a further cutting guide. There is a corresponding slot in the body part 212. Second end plate 230 is attached by a pivot mechanism (not shown) to the main body 212. A pair of threaded members (of which only member 242 can be seen) can be operated to pivot end plate 230 thereby altering the angle of slot 238 relative to body 212. In use, slot 238 provides a cutting guide by which a femoral distal cut can be made using a saw when instrument 210 is attached to a femur in use.

Generally, the threaded members can be adjusted to change the position of the cutting guides 214, 216, 218, 220, 221 relative to the distal end of a femur so that the position of the femoral cuts can be adjusted as required to provide soft tissue balancing.

The amounts of adjustment can be marked on the screws and guides and can be determined manually from a look up table or from a computer controlled tissue balancing measurement.

Figure 18:
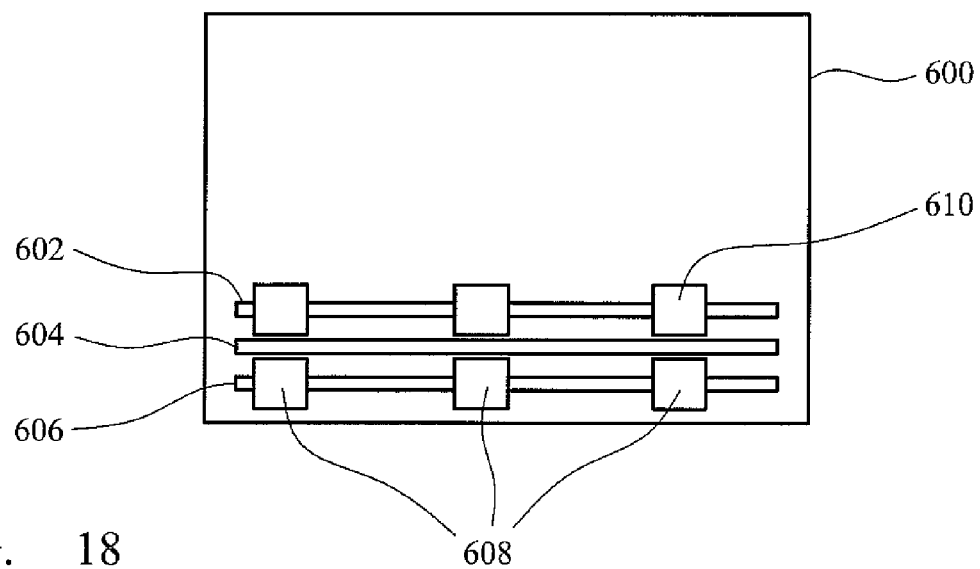
FIG. 18 shows a view of an adjustment mechanism which can be used in an instrument according to the invention.

As illustrated in FIG. 18, in another embodiment of the instrument adjustability is simply achieved through offering multiple slots in the body for the same cut to remove more or less bone stock. Break-off barriers can be provided over the unplanned slots so that the surgeon has to deliberately do something in order to use them.

FIG. 18 shows a part of the instrument 600 which includes three slots, 602, 604, 606, providing cutting guides for making the same cut. However, a single or multiple (as illustrated) push fit inserts 608, 610 are used to block the slots that are normally not used so that only a single slot is initially available for making the cut. The position of the slot to be used for making the cut can then be adjusted by removing the inserts from another of the slots so that that slot can then be used for making the cut in a preferred position. The inserts can be colour coded to easily identify the direction of the slot displacement.

In another embodiment of the instrument the points/features/surfaces on the bones are selected such that they are outside the surfaces being removed. The instrument is then uniquely re-locatable even after the initial cuts are made. This is particularly useful for a surgeon who uses a measured resection approach and who wants to make all his cuts and check afterwards. This allows him to remount his cutting guides and make any adjustments he sees as necessary.

The invention can be adapted for resection of any bone or hard-body material and flat-cut implant type. For example, for the tibia the complexity can be reduced due to a single cut being used. The invention can also be applicable to preparing round surfaces for any type of implant, in which case a burr can be used to remove the material.

Figure 19:
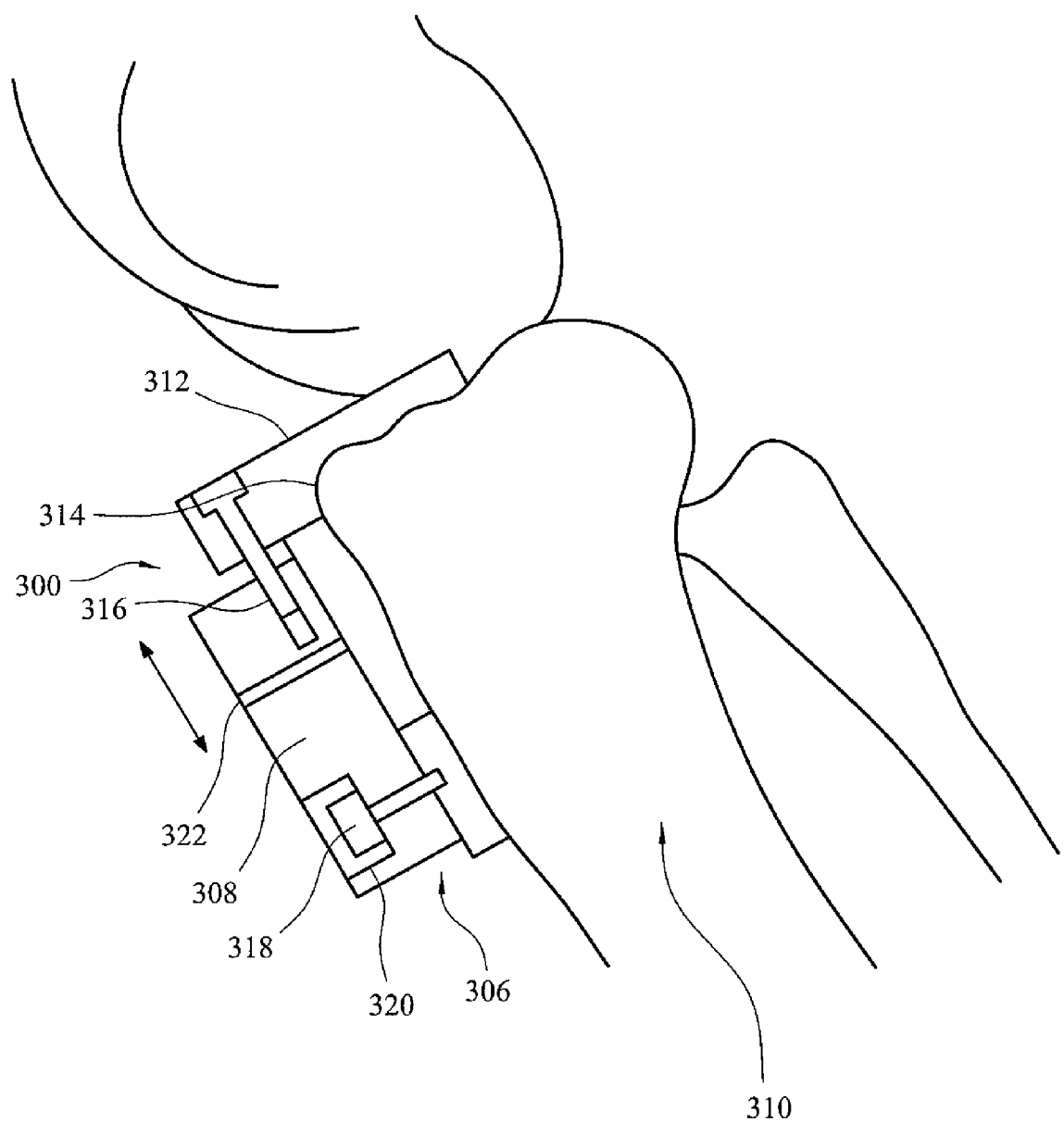
FIG. 19 shows a schematic cross sectional view through a seventh embodiment of a surgical instrument according to the invention.

FIG. 19 shows a schematic side view in the sagittal plane of a further embodiment 300 of the invention providing an adjustable tibia cutting instrument. The instrument 306 includes a main body section 308 with a cutting slot 322 through which a saw blade can be guided to make a tibial cut. Instrument 306 is attached to the surface of the tibia bone 310 by an attachment part 312 having a surface shape matching the shape of the surface of a corresponding region 314 of the patient's tibia 310. A screw mechanism 316 can be operated to adjust the position of the cutting slot 322 in the proximal-distal direction. A second screw mechanism 318 is also provided which can be operated to change the slope of the cut by allowing the guide to pivot in the varus-valgus direction about it.

Figure 20:
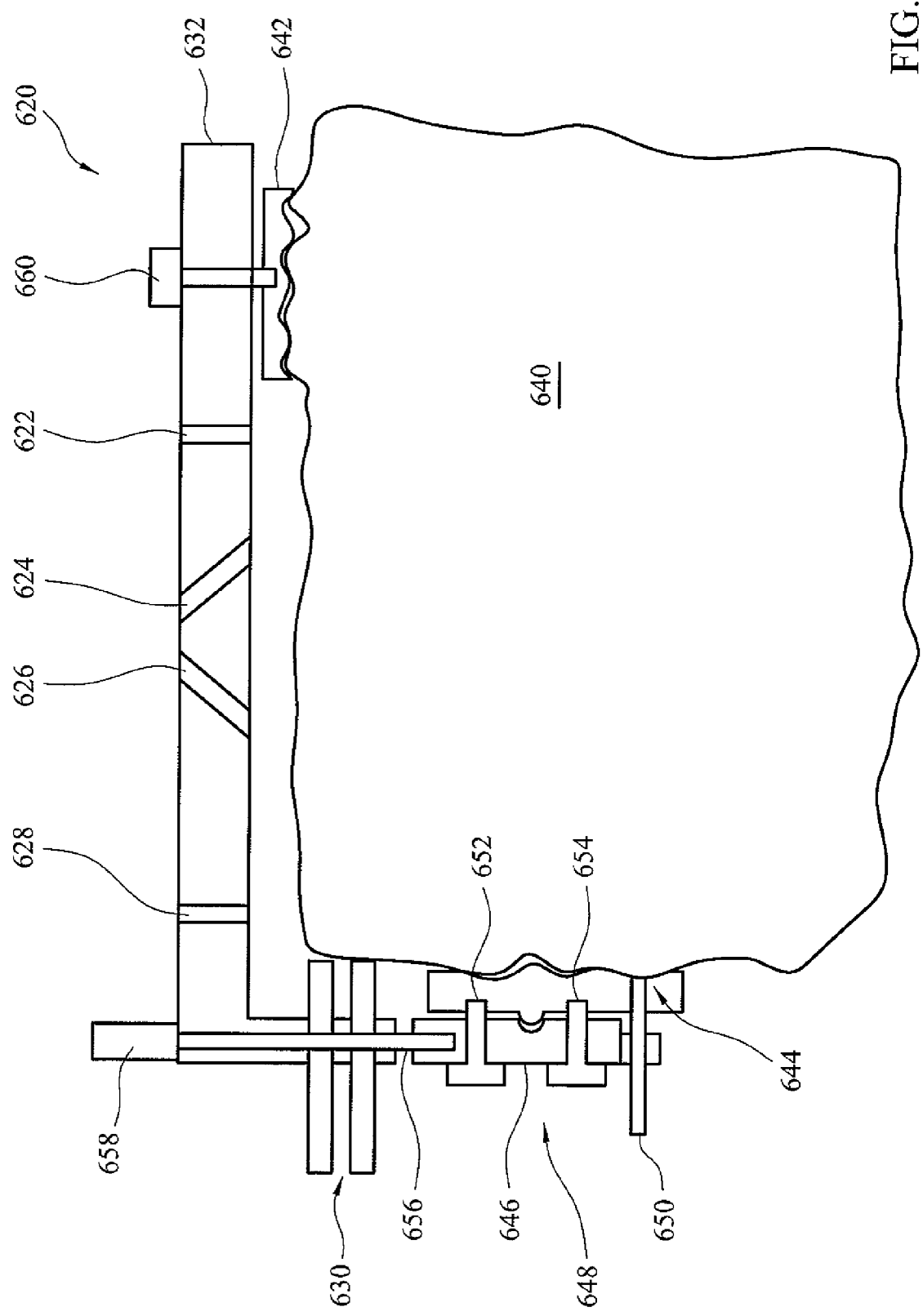
FIG. 20 shows a schematic cross sectional view of a further embodiment of an instrument according to the invention.

FIG. 20 shows a further variation of an instrument according to the invention similar to the instruments shown in FIGS. 16, 17 and 19. The instrument 620 has a plurality of slots 622, 624, 626, 628, 630 providing cutting guides. A main body 632 of the instrument is mounted on the bone 640 by an attachment area component 642 which has a surface form matching the patient's bone shape. The component 642 is attached to the body 632 by an adjustment screw 660 so that the instrument can be stabilised during cutting and after the position of the instrument has been adjusted. However, the surfaces of the bone and attachment area will not match exactly after angular or linear adjustment. The bone surface is typically cut away for distal or proximal cuts so adjustment for stabilisation is not always necessary after the block instruments position has been adjusted.

The other patient specific attachment area 644 is attached to a further part 646 of the instrument by a pivot mechanism 648 to allow some rotation of the instrument relative to the bone 640. The pivot mechanism includes two screws. Threaded bores are provided in foot component 644 into which free ends 652, 654 of the screws engage. Apertures are provided in part 646 to receive the screw shanks but are a loose fit to allow some pivoting movement. The end of foot component 644 provides an end stop to prevent over rotation of the body. A bone pin 650 passing through an aperture in the foot component 644 prevents the foot component 644 moving relative to the bone.

If both screws are operated in the same sense, then the instrument simply translates. However, if only one screw is operated, or the two screws are operated in opposition senses, then the main body of the instrument will pivot or tilt thereby providing some angular adjustment of the position of the instrument. The pivot mechanism allows screw driven rotation of plus or minus approximately 2E. In an alternate arrangement, a single screw and a flexible hinge can be used to provide the pivot mechanism. Measured rotations in between 2E steps can be achieved by measure turns of the screws.

Part 646 is itself mounted on a screw thread 656 so that the remainder of the main body 632 can be moved toward and away from the bone by operating thread 656 using head 658 and operating adjustment screw 660.

Figure 21A:
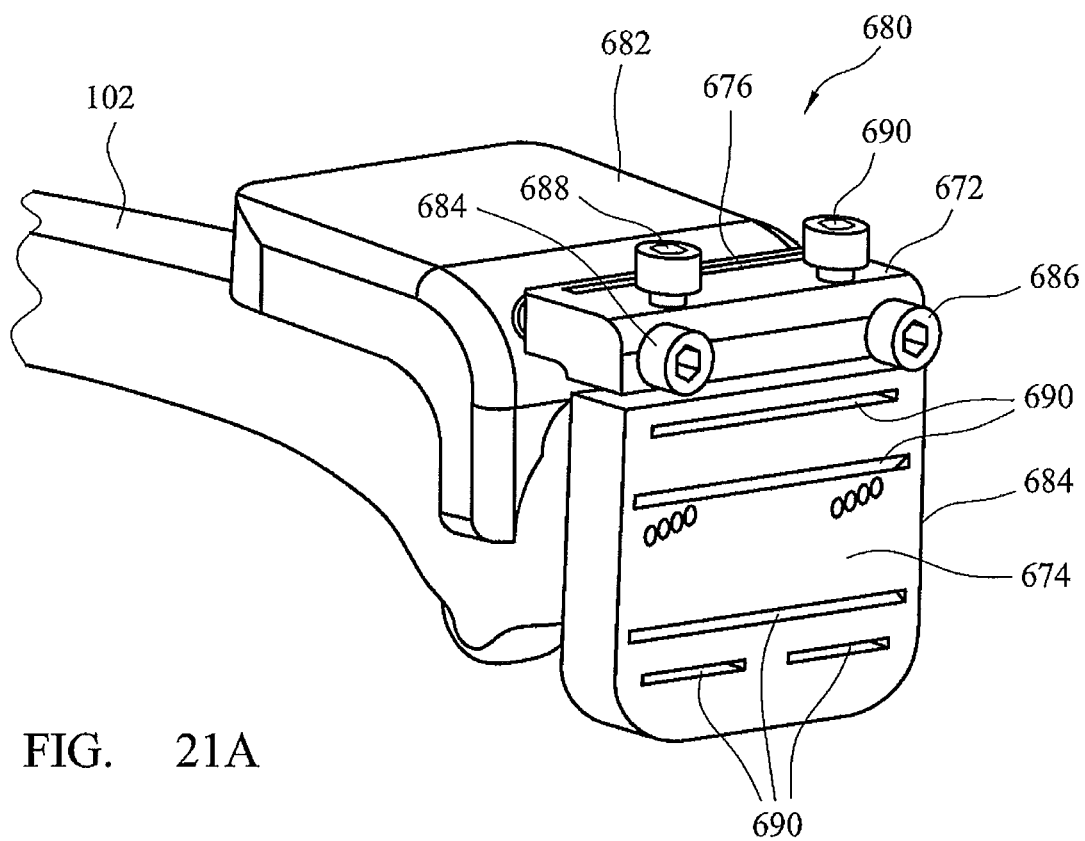
FIGS. 21A and 21B show perspective views of a further embodiment of an instrument according to the invention.
Figure 21B:
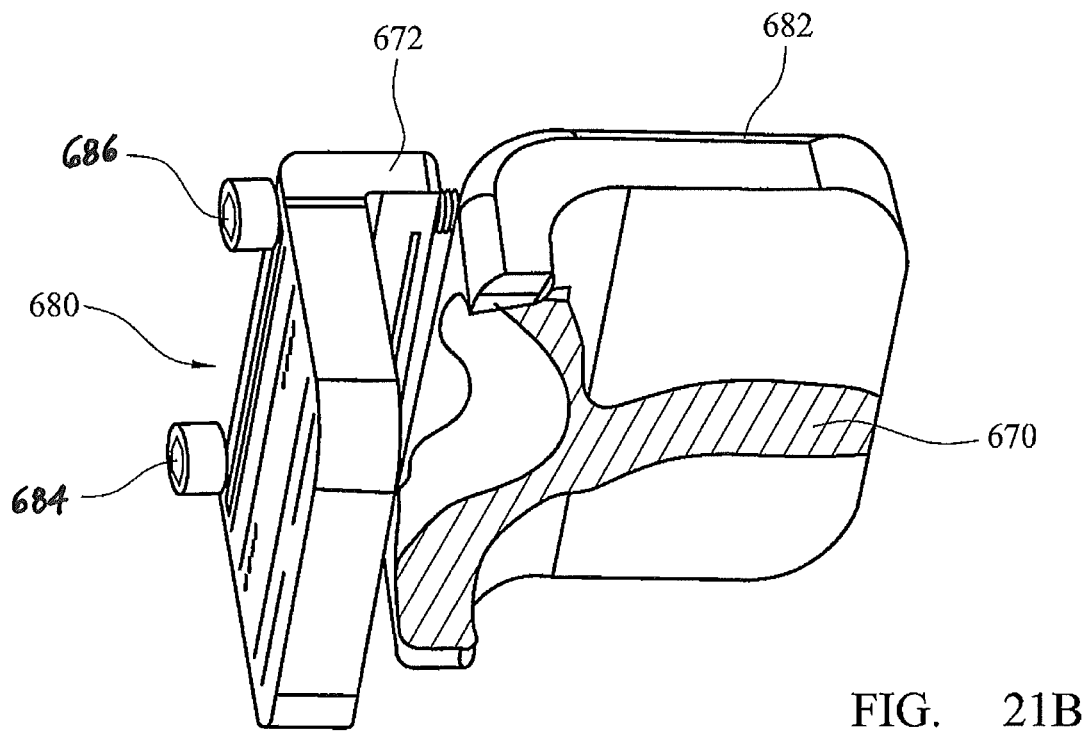

FIGS. 21A and 21B show perspective views of a further instrument 680 being an embodiment of the invention similar to those shown in FIGS. 16, 17, 19 and 20. FIG. 21B shows a perspective view from a bone engaging side of the instrument 680 and FIG. 21A shows the instrument mounted on a femur 102 in use. The instrument 680 has a first bone engaging portion 682 and a second portion 684 which includes a plurality of slots defining cutting guides for making a plurality of cuts typically used when preparing a femur to receive an implant. The first and second portions between them comprise the body of the instrument.

The bone engaging portion has a bone facing side which includes a surface 670 extending over the bone facing side and which provides an extended bone attachment area whose shape matches the patient specific shape of the surface of a corresponding part of the surface of the patient's bone. Hence, the bone engaging portion is the only part of the instrument that engages the bone and ensures that the instrument is mounted on the bone at a unique pre-selected position.

The cutting guide bearing portion 684 of the instrument has first 672 and second 674 portions, each bearing portion has at least one slot. Portion 672 has a slot 676 for guiding the making of a distal cut. Portion 672 is attached to the bone engaging portion 682 by a pair of threaded screws 684, 686 which are captured so that operation of the screws causes the first and second portions to translate in the distal-proximal direction relative to the bone 102 thereby allowing the position of the distal cut to be adjusted.

The second portion includes five slots 690 which can be used to guide the making of anterior and posterior cuts and angled cuts typically used when preparing a femur during knee arthroplasty procedures. Portion 674 is attached to the first portion 672 by a further pair of threaded screws 688, 690 which are captured so that operation of the screws causes the first and second portions to translate in the anterior posterior direction relative to the bone 102 thereby allowing the position of various of the cuts to be adjusted.

FIGS. 22A, 22B and 22C show perspective views of part of a further embodiment of an instrument 700 according to the invention. The instrument 700 is generally similar to that shown in FIGS. 3, 8 and 12. The instrument has a different type of adjustment mechanism. The adjustment mechanism involves the use of inserts or attachments with slots in defining the cutting guides. The slots in different inserts and attachments are offset by different amounts and so allow the position of the cutting guide to be adjusted relative to the bone to which the instrument is attached.

For example, FIG. 22A shows a perspective top view of the main body part 701 of an instrument 700 and includes a large rectangular recess 702 in the main body and having an aperture 704 passing through the body and providing access to the bone beneath the instrument in use. The recess includes a shoulder 706 extending around a part of the recess and which acts to control the depth of insertion of an insert 710 as illustrated in FIG. 22B. The insert is a metal block which includes a slot 712 passing through the block. The recess and insert are dimensioned and shaped so that the block mates with the recess in a push-fit manner to securely attach the insert to the main body of the instrument. The insert acts as a shim to control the position of the slot and hence cutting guide. A set of inserts are provided having different amounts of offset of the slot and also having slots at different angles so that a particular insert can be selected and used so as to adjust the position and/or direction of the cut as defined by the selected insert.

As illustrated in FIG. 22C a plurality of inserts or attachments can be provided as part of the instrument 700. For example a cutting guide insert or attachment 714 can be provided that co-operates with formations adjacent feet 716 and 718 to allow the insert 714 to be push-fit attached to a side of the instrument 700. Insert 714 includes a slot 715 providing a cutting guide which can be used when making a distal femoral cut. A particular insert with a selected off set slot position or slot angle is selected and inserted in the instrument body in order to adjust the position of the cut to be made.

The inserts or shims 710, 714 are generally made available with different lateral and angular offsets to permit adjustment of the cut surface after the soft-tissue measurement or other appropriate adjustments are made based on intra-operative or pre-operative information. The recess 702 is wide enough to allow for the expected variation in the cutting surfaces. The shims are inserted into the main body after any adjustment calculations have been made. The shims are re-usable and their simple form allows for easy sterilization and use across a range of sizes and cutting positions in the patient specific main body 701. One end of the recess 706 can be left open to allow for inserts longer than the slot, e.g. for patients with small bones, to be used.

Figure 22D:
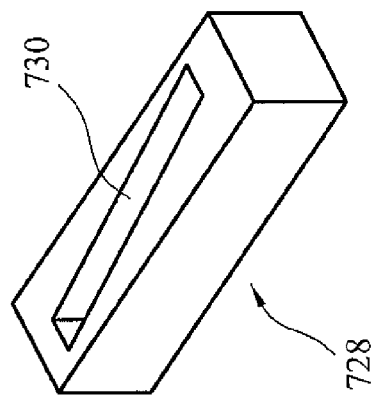
Figure 22E:
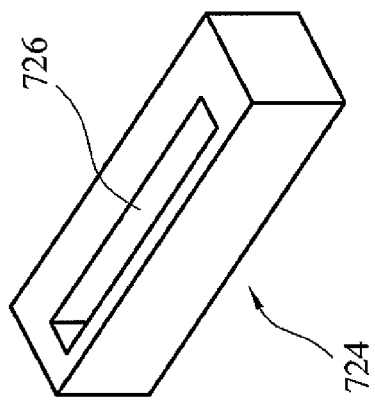
Figure 22F:
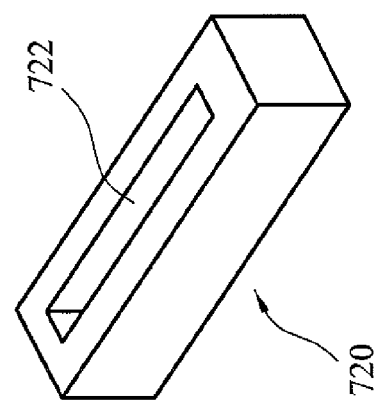

FIGS. 22D, 22E and 22F show examples of different insert blocks by way of further explanation of how they can be used to adjust the cutting instrument. FIG. 22D shows a an insert block 720 having a slot aperture 722 extending along and parallel to the longitudinal axis of the block. By using this block instead of block 712, the position of the resulting cut can be adjusted in the anterior-posterior direction. Insert block 724 shown in FIG. 22E has a slot aperture 726 again extending along and parallel to the longitudinal axis of the block 724, but the slot is closer to a side of the block 724 compared to block 720. Hence, by using this block in a first orientation, or second 180E rotated direction, in place of block 720, the position of the resulting cut can be changed in the anterior-posterior direction. FIG. 22F shows a an insert block 728 having a slot aperture 730 extending generally along the longitudinal axis of the block, but not parallel to the longitudinal axis of the block. Hence block 728 can be inserted into the instrument and used in order to adjust the angular position of the resulting cut.

Two sets of colour-coded inserts or blocks are provided made of a hard material. The first set of blocks is used for making the anterior, posterior, distal and proximal cuts.

These cuts can vary in their rotation (Varus-Valgus) and lateral positioning. In typical use, the implant can be moved laterally up to +/−3 mm in steps of 1.5 mm. To provide this degree of cut adjustment three blocks are used, a first with neutral positioning of the slot, a second with a 1.5 mm offset of the slot and a third with a 3 mm offset of the slot. It can also be helpful to provide blocks with various amounts of variation of the varus-valgus angle, for example 0, 1, 3 or 5 degrees. Hence, by also providing insert blocks with slots which yaw and pitch it is possible to cover all values of Varus-Valgus and lateral movement with, e.g., twelve blocks.

The second set of blocks is used for making the chamfer cuts. A similar recess for receiving the insert blocks is used for the chamfer cuts and, for both of the chamfer cuts, the recess is aligned with the chamfer angle. The insert blocks in the second set are slightly longer than the blocks of the first set and do not go as deep into the body of the instrument. They can be held in a stable position, since the recesses for receiving the insert blocks for the chamfer cuts and the anterior, posterior and distal cuts will overlap in the femur. Again twelve blocks can be used to cover all of the displacement combinations (for chamfers at 45°) and for other angles of chamfers twenty four blocks can be used.

Figure 23:
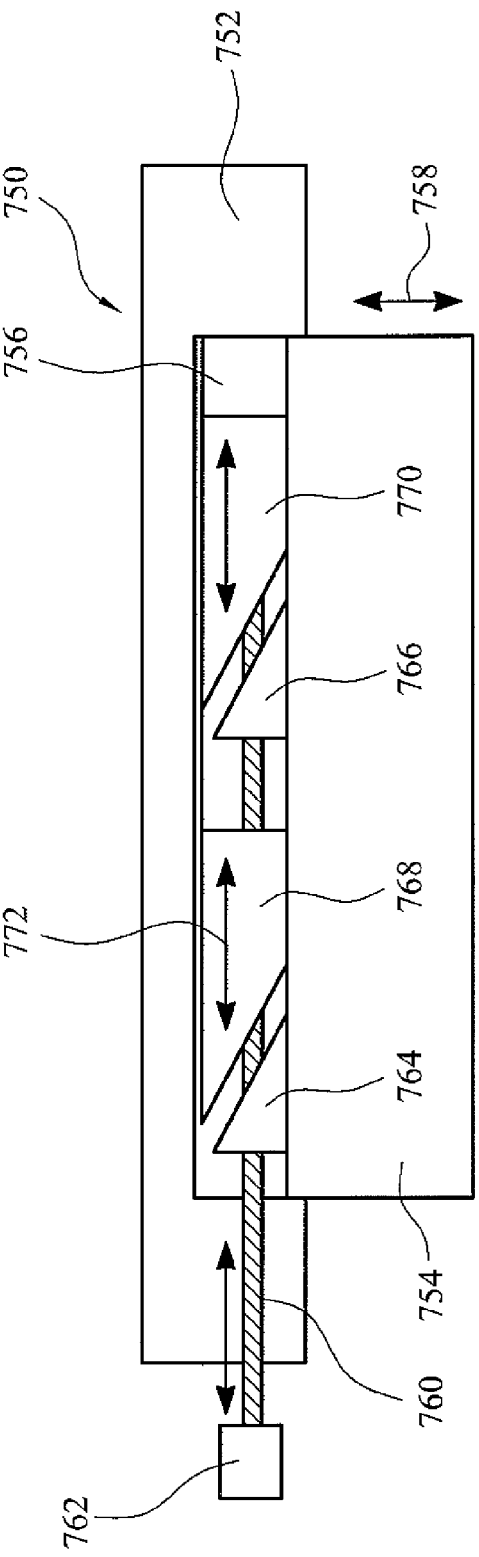
FIG. 23 shows a schematic cross sectional view of a further adjustment mechanism which can be used in an instrument according to the invention.

FIG. 23 shows a schematic cross section through an embodiment of a further adjustment mechanism 750 that can be used in the instrument of the invention. A first part 752 of the adjustment mechanism is a part of the main body of the instrument and a second part 754 of the adjustment mechanism bears a member or foot including an attachment area (not shown) of the instrument. Part 752 defines a hollow portion 756 into which part 754 can slidingly engage in a direction as illustrated by double headed arrow 758. A threaded shaft 760 has a head 762 at a free end and passes through a first pair of wedge shaped members 764, 766 which are stationary and a second set of wedge shaped members 770 which are movable and can be driven back and forth in a direction illustrated by double headed arrow 772 by rotating thread 760. As wedges 764, 766 are stationary, when driven toward them by rotation of thread 760 of the drive mechanism, the slanted end faces of wedges 768, 770 will ride onto and slide up the slanted faces of the wedges 764, 766 and the second part 754 will be driven out of and away from hollow portion 756, thereby increasing the separation between the main body and the attachment areas and so adjusting the position of the cutting guides borne by the main body.

By using this adjustment mechanism 750, the joint volume itself does not have to contain any adjustment screws and the overall instrument can be made more compact. Screw 760 moves the moveable members 768, 770 in the anterior-posterior direction to cause up/down movement of wedges 764, 766 and hence the attachment areas are also caused to move up and down. No tool is required for adjustment in the proximal distal direction and this mechanism provides more compact control particularly useful in minimally invasive surgery (MIS) procedures. A return force can be provided by the surgeon pressing on the instrument body.

Figure 24A:
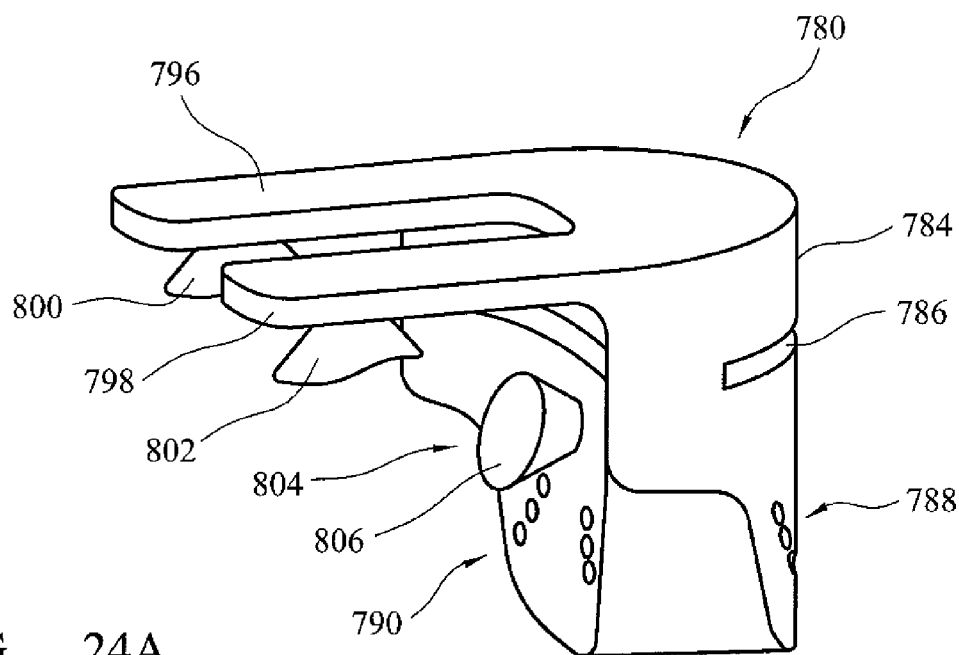
FIGS. 24A and 24B show perspective views of a further embodiment of an instrument according to the invention.
Figure 24B:
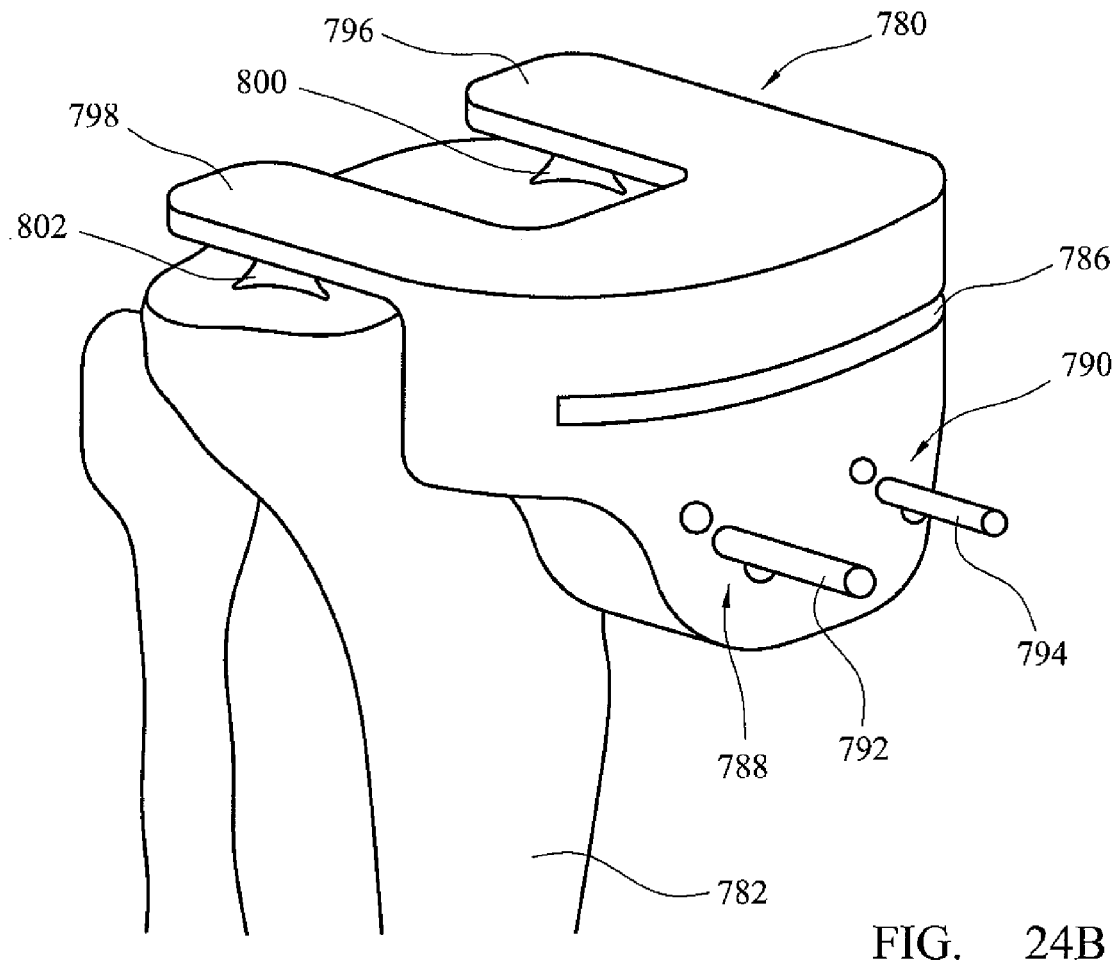

FIGS. 24A and 24B show perspective views of a further embodiment of an instrument according to the invention. FIG. 24A shows a perspective view from a rear side of the instrument 780 and FIG. 24B shows a perspective view from a front side of the instrument 780 mounted on a tibia 782 in use. The body 784 of the instrument includes a slot 786 passing through the body and providing a cutting guide for receiving a cutting device for making a tibial cut in use. Two groups 788, 790 of three apertures pass through the body for receiving bone pins 792, 794 for securing the instrument to the tibia in use 782. A pair of arms 796, 798 extend from the main body and bear a first patient specific shaped member 800 and a second patient specific shaped member 802 on a bone facing underside of the arms, each member 800, 802 providing an attachment surface configured to engage with the patient's bone as best seen in FIG. 24B. A bone facing side of the main body bears a third patient specific shaped member 804 providing a further attachment surface 806 for configured to match the shape of an area on the anterior surface of the tibia 782 in use.

The instrument is used similarly to similar embodiments described above. Initially the instrument is mounted on the tibia by engaging the attachment areas with the bone surface so as to initially locate the instrument at a predetermine position. Bone pins 792, 794 are then introduced via holes 788, 790 to secure the instrument to the tibia. If adjustment of the position of the cut defined by the slot 786 is required for any reason, then the instrument 780 is removed from the bone pins and the members 800, 802, 804 removed from the instrument and then the instrument can be replaced on the tibia on the bone pins using different ones of the holes 788, 790 so as to move the slot upward or downward in the proximal-distal direction so as to adjust the height of the tibial cut. In general, the embodiments shown in the Figures can be used in a number of different surgical workflows. As mentioned briefly above, prior to beginning the surgical procedure, a patient-specific instrument is manufactured, for example, using a rapid prototyping technique, so that the attachment areas of the instrument are patient-specific and allow the instrument to be uniquely attached to the patient's bone. This can be achieved using various types of data describing the geometry or shape of the patient's bone, for example, derived from CT scan data. For example, the first, second, fourth and fifth embodiments use unique negative shapes which allow them to be fitted to the patient-specific bone surface. These shapes can cover the complete bone surface or selected parts thereof where the geometry is accessible. The second approach is more appropriate where soft tissue is attached to the bone (e.g. cartilage) which cannot accurately be modelled in a pre-operative planning step.

For the tibia, the most important changes to cuts in order to accommodate soft tissue balancing are being able to increase or decrease the tibial slope, being able to move the tibial cut in a more distal or proximal direction and being able to adjust the varus-valgus angle.

For the femur, the most important changes to cuts in order to accommodate the soft tissue balancing are being able to move the femoral cut in the anterior or posterior direction. It is also important to be able to move the distal femoral cut in a more proximal direction. It is also useful to be able to change the varus-valgus angle on the femur. It is also beneficial to be able to change the internal/external rotation.

In a first workflow, initially the tibial cut is made according to the planned surgical procedure. Then, a determination is made of potential changes in order to improve the flexion and extension gap, either using a tool or by visual inspection and experience of the surgeon. The instrument is then attached and adjusted as required so that the resulting cut will provide the required flexion and extension gaps.

In an alternative workflow, the tibial and femoral cuts are made according to the planned procedure. Trial implants are applied and then spacers, can be used to assess the flexion and extension gap. Then, the instrument can be applied to the cut tibia and femur and adjusted to allow further corrective cuts to be made as required, in order to provide the desired flexion and extension gap. However, this approach will miss the corrections available for the femur by simply moving the distal femoral cut in a more proximal direction. However, for the tibia all adjustments are still available. In this case standard spacer elements (that match the cut surface) can be inserted between the instrument and the cut-bone surface. Some of these will replace the surface matching areas, other surface-matching areas on bone that has not been removed will remain as before.

A number of different features have been described above in connection with a number of different embodiments of the instrument of the invention. It will be appreciated that features of the different embodiments can be used additionally or alternatively with features of others of the embodiments so as to arrive at further instruments according to the invention. For example, some of the different adjustment mechanisms described can be used with others of the adjustment mechanisms described in the same instrument so as to provide the required translational and/or angular adjustment of the instrument. Also, different adjustment mechanisms and/or combinations of adjustment mechanisms can be used with instruments intended for use with different bones or for making different cuts. Further, the invention is not limited to only femoral or tibial instruments and can be used on a variety of different bones, where it would be helpful to be able to adjust the position of a cut from an intended initial position.

The invention claimed is:

1. A surgical instrument for use in an orthopaedic arthroplasty procedure to be carried out on a bone of a patient having an uncut bone surface, comprising:

a body including a patient specific bone engaging portion and a cutting guide portion, wherein the patient specific bone engaging portion and the cutting guide portion are independent from one another, the bone engaging portion including a body surface that has at least one attachment area, the at least one attachment surface area having a contoured negative shape that matches a specific shape of a surface of an area of the uncut bone surface of the patient, wherein the at least one attachment surface area is configured to matingly engage with the surface area of the uncut bone surface to locate the at least one attachment area in a unique, predetermined position with respect to the bone;

wherein the body surface comprises at least one member that extends therefrom, the at least one member being shaped so as to maintain a defined separation between the cutting guide portion and the bone when a position of the cutting guide portion is changed, the cutting guide portion including a first portion and a second portion, wherein the first portion and the second portion of the cutting guide portion are independent from one another, the first portion including at least a first cutting guide attached to the first portion of the cutting guide portion of the body, the first cutting guide defining a first cutting plane along which the bone is to be resected when the at least one attachment area is located in the unique, predetermined position with respect to the bone, the second portion including a second cutting guide attached to the second portion of the cutting guide portion of the body, the second cutting guide defining a second cutting plane along which the bone is to be resected when the at least one attachment area is located in the unique, predetermined position with respect to the bone, each of the first and second portion including opposite planar outer and inner surfaces through which the first and second cutting plane extends, respectively;

wherein each of the first and second cutting guides is configured to receive and guide a saw blade for resecting the bone of the patient, a first adjustment mechanism extending between the first portion of the cutting guide portion and the patient specific bone engaging portion and operable to attach the first portion of the cutting guide portion to the patient specific bone engaging portion and to lockably change a position of the first portion of the cutting guide portion with respect to the patient specific bone engaging portion in a first direction, and to change a position of the first cutting plane relative to the bone when the at least one attachment area is located in the unique, predetermined position and matingly engages the surface area of the uncut bone surface; and a second adjustment mechanism extending between the first portion of the cutting guide portion and the second portion of the cutting guide portion and operable to attach the first portion of the cutting guide portion to the second portion of the cutting guide portion and to lockably change a position of the second portion of the cutting guide portion with respect to the first portion of the cutting guide portion in a second direction and to change a position of the second cutting plane relative to the bone when the at least one attachment area is located in the unique, predetermined position and matingly engages the surface area of the uncut bone surface; wherein:

the first cutting plane intersects the second cutting plane;

the first direction is perpendicular to the second direction, the first adjustment mechanism comprises a plurality of adjustment screws by which the first portion of the cutting guide portion of the body is attached to the bone engaging portion of the body; and the second adjustment mechanism comprises a plurality of adjustment screws by which the second portion of the cutting guide portion of the body is attached to the first portion of the cutting guide portion of the body.

2. The instrument of claim 1, wherein the first adjustment mechanism translates the first portion of the cutting guide portion with respect to the patient specific bone engaging portion to thereby translate the first cutting plane relative to the patient specific bone engaging portion and the second adjustment mechanism translates the second portion of the cutting guide portion with respect to the first portion of the cutting guide portion to thereby translate the second cutting plane relative to the patient specific bone engaging portion.

3. The instrument of claim 1, wherein the first cutting plane is perpendicular to the second cutting plane.

4. The instrument of claim 1, wherein the first adjustment mechanism is operable to move the first cutting plane in a proximal-distal direction relative to the patient specific bone engaging portion and the second adjustment mechanism is operable to move the second cutting plane in an anterior-posterior direction relative to the patient specific bone engaging portion.

5. The instrument of claim 1, wherein at least one portion of the cutting guide portion includes a plurality of different cutting guides.

6. The instrument of claim 1, wherein the uncut bone surface is part of an anterior surface of the distal femur, and the at least one attachment surface area is configured to negatively engage the uncut bone surface of the anterior surface of the distal femur.

* * * * *